(12) United States Patent
Vandyck et al.

(10) Patent No.: US 9,382,261 B2
(45) Date of Patent: *Jul. 5, 2016

(54) SUBSTITUTED QUINAZOLINONES AS HCV INHIBITORS

(71) Applicant: Janssen R&D Ireland, Co Cork (IE)

(72) Inventors: Koen Vandyck, Paal-Beringen (BE); Pierre Jean-Marie Bernard Raboisson, Rosieres (BE)

(73) Assignee: Janssen Sciences Ireland UC, Little Island Co Cork (IE)

( * ) Notice: Subject to any disclaimer, the term of this patent is extended or adjusted under 35 U.S.C. 154(b) by 21 days.

This patent is subject to a terminal disclaimer.

(21) Appl. No.: 14/368,511

(22) PCT Filed: Dec. 27, 2012

(86) PCT No.: PCT/EP2012/076942
§ 371 (c)(1),
(2) Date: Jun. 25, 2014

(87) PCT Pub. No.: WO2013/098320
PCT Pub. Date: Jul. 4, 2013

(65) Prior Publication Data
US 2014/0378485 A1     Dec. 25, 2014

(30) Foreign Application Priority Data

Dec. 28, 2011 (EP) .................. 11195841
Jan. 24, 2012 (EP) .................. 12152267

(51) Int. Cl.
| | |
|---|---|
| *A61K 31/517* | (2006.01) |
| *C07D 239/88* | (2006.01) |
| *C07D 491/113* | (2006.01) |
| *C07D 403/14* | (2006.01) |
| *A61K 45/06* | (2006.01) |

(52) U.S. Cl.
CPC .......... *C07D 491/113* (2013.01); *A61K 31/517* (2013.01); *A61K 45/06* (2013.01); *C07D 403/14* (2013.01)

(58) Field of Classification Search
CPC .................... A61K 31/517; C07D 239/88
USPC .............. 514/266.31; 544/287; 548/335.1
See application file for complete search history.

(56) References Cited

FOREIGN PATENT DOCUMENTS

| | | |
|---|---|---|
| WO | WO 2006/133326 A1 | 12/2006 |
| WO | WO 2008/021927 A2 | 2/2008 |
| WO | WO 2008/021928 A2 | 2/2008 |
| WO | WO 2008/048589 A2 | 4/2008 |
| WO | WO 2008/070447 A2 | 6/2008 |
| WO | WO 2010/017401 A1 | 2/2010 |
| WO | WO 2010/065681 A1 | 6/2010 |
| WO | WO 2011054834 A1 | 5/2011 |
| WO | WO 2012/013643 A1 | 2/2012 |

OTHER PUBLICATIONS

Lohmann et al., "Replication of Subgenomic Hepatitis C Virus RNAs in a Hepatoma Cell Line" 1999, Science, 285:110-113.
Kreiger et al., "Enhancement of Hepatitis C Virus RNA Replication by Cell Culture-Adaptive Mutations", (2001) Journal of Virology 75: 4614-4624.
Lohmann et al., "Viral and Cellular Determinants of Hepatitis C Virus RNA Replication in Cell Culture", (2003) Journal of Virology 77: 3007-3019.
Yi et al., "Adaptive Mutations Producing Efficient Replication of Genotype 1a Hepatitis C Virus RNA in Normal Huh7 Cells", (2004) Journal of Virology 78: 7904-7915.
Chinese Search Report for corresponding application CN201280065174.5 dated Jul. 13, 2015.

*Primary Examiner* — Douglas M Willis
(74) *Attorney, Agent, or Firm* — Andrea Jo Kamage

(57) ABSTRACT

Inhibitors of HCV replication of formula (I) including stereochemically isomeric forms, salts, and solvates thereof, wherein R and R' have the meaning as defined herein. The present invention also relates to processes for preparing said compounds, pharmaceutical compositions containing them and their use, alone or in combination with other HCV inhibitors, in HCV therapy.

(I)

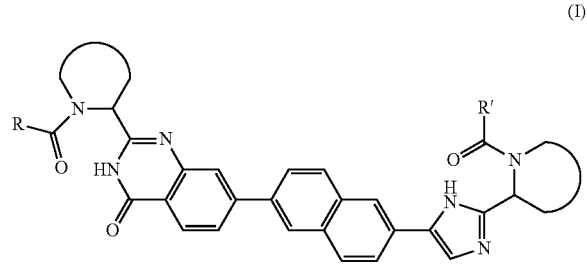

9 Claims, No Drawings

SUBSTITUTED QUINAZOLINONES AS HCV INHIBITORS

CROSS-REFERENCE TO RELATED APPLICATIONS

This application is a 371 of International Application Number PCT/EP2012/076942, filed 27 Dec. 2012, which claims the benefit of Application Number EP11195841.9, filed 28 Dec. 2011 and EP12152267.6, filed 24 Jan. 2012. The entire contents of each of the aforesaid applications are incorporated herein by reference in their entirety.

FIELD OF THE INVENTION

This invention relates to hetero-bicyclic derivatives, in particular quinazolinone derivatives, which are inhibitors of the hepatitis C virus (HCV), their synthesis and their use, alone or in combination with other HCV inhibitors, in the treatment or prophylaxis of HCV.

DESCRIPTION OF RELATED ART

HCV is a single stranded, positive-sense RNA virus belonging to the Flaviviridae family of viruses in the hepacivirus genus. The viral genome translates into a single open reading frame that encodes for multiple structural and non-structural proteins.

Following the initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis, leading to cirrhosis, end-stage liver disease, and HCC (hepatocellular carcinoma), making it the leading cause of liver transplantations.

There are six major HCV genotypes and more than 50 subtypes, which are differently distributed geographically. HCV genotype 1 is the predominant genotype in Europe and in the US. The extensive genetic heterogeneity of HCV has important diagnostic and clinical implications, perhaps explaining difficulties in vaccine development and the lack of response to current therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

Current HCV therapies are based on (pegylated) interferon-alpha (IFN-α) in combination with ribavirin. This combination therapy yields a sustained virologic response in 40% of patients infected by genotype 1 HCV and about 80% of those infected by genotypes 2 and 3. Beside the limited efficacy on HCV genotype 1, this combination therapy has significant side effects including influenza-like symptoms, hematologic abnormalities, and neuropsychiatric symptoms. Hence there is a need for more effective, more convenient and better-tolerated treatments.

Experience with HIV drugs, in particular with HIV protease inhibitors, has taught that sub-optimal pharmacokinetics and complex dosing regimens quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$, is essential to slow down the development of drug escape mutants. Achieving the pharmacokinetics and rate of drug metabolism necessary to allow such trough levels provides a stringent challenge to drug design.

The NS5A protein of HCV is located downstream of the NS4B protein and upstream of the NS5B protein. Upon post-translational cleavage by the viral serine protease NS3/4A, the NS5A matures into a zinc containing, three-domain phosphoprotein that either exists as a hypophosphorylated (56-kDa, p56) or hyperphosphorylated species (58-kDa, p58). NS5A of HCV is implicated in multiple aspects of the viral lifecycle including viral replication and infectious particle assembly as well as modulation of the environment of its host cell. Although no enzymatic function has been ascribed to the protein it is reported to interact with numerous viral and cellular factors.

A number of patents and patent applications disclose compounds with HCV inhibitory activity, in particular targeting NS5A. WO2006/133326 discloses stilbene derivatives while WO 2008/021927 and WO 2008/021928 disclose biphenyl derivatives having NS5A HCV inhibitory activity. WO 2008/048589 discloses 4-(phenylethynyl)-1H-pyrazole derivatives and their antiviral use. WO 2008/070447 discloses a broad range of HCV inhibiting compounds including a benzimidazole moiety. WO-2010/017401 and WO-2010/065681 both disclose bis-imidazole inhibitors of HCV NS5A.

BRIEF SUMMARY OF THE INVENTION

There is a need for HCV inhibitors that may overcome the disadvantages of current HCV therapy such as side effects, limited efficacy, the emerging of resistance, and compliance failures, as well as improve the sustained viral load response.

The present invention concerns a group of HCV inhibiting quinazolinone derivatives, with useful properties regarding one or more of the following parameters: antiviral efficacy, favorable profile of resistance development, reduced or lack of toxicity and genotoxicity, favorable pharmacokinetics and pharmacodynamics, ease of formulation and administration, and limited or lack of drug-drug interactions with other drug substances, in particular other anti-HCV agents.

Compounds of the invention may also be attractive due to the fact that they lack activity against other viruses, in particular against HIV. HIV infected patients often suffer from co-infections such as HCV. Treatment of such patients with an HCV inhibitor that also inhibits HIV may lead to the emergence of resistant HIV strains.

DETAILED DESCRIPTION OF THE INVENTION

In a first embodiment, the present invention provides a subgroup of compounds of formula I, which can be represented by the formula (I);

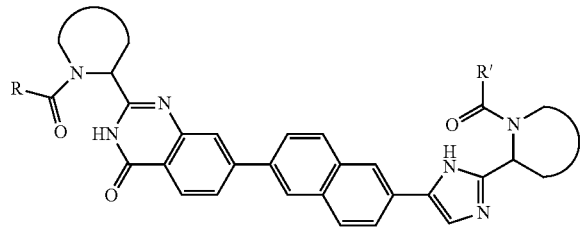

or a stereoisomer thereof, wherein:
at least one of

independently is selected from a group comprising

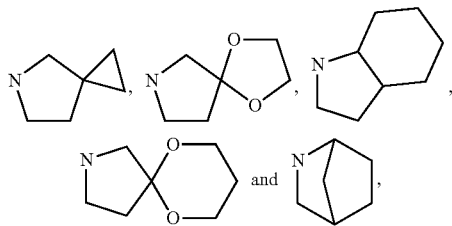

and the other

is selected from the group additionally comprising

R and R' are independently selected from —CR$_1$R$_2$R$_3$, aryl optionally substituted with 1 or 2 substituents selected from halo and methyl, or heterocycloalkyl, wherein
  R$_1$ is selected from C$_{1-4}$alkyl; C$_{2-4}$alkyl substituted with methoxy or hydroxyl; and phenyl optionally substituted with 1 or 2 substituents independently selected from halo and methyl;
  R$_2$ is hydroxyl, amino, mono- or di-C$_{1-4}$alkylamino, C$_{1-4}$alkyl-carbonylamino, C$_{1-4}$alkyloxycarbonylamino;
  R$_3$ is hydrogen or C$_{1-4}$alkyl;
or a pharmaceutically acceptable salts or a solvate thereof.

In a preferred embodiment,

independently is selected from a group comprising

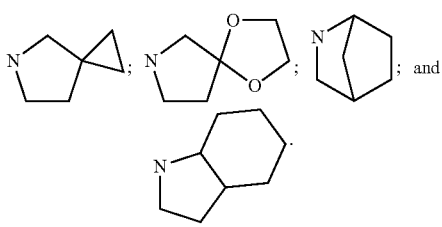

Even more preferred is a compound of formula I wherein at least one

independently is

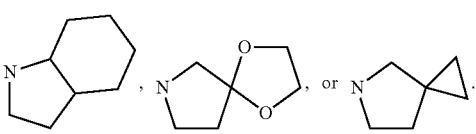

More preferably compounds of the invention provides compounds which can be represented by the formula Ia

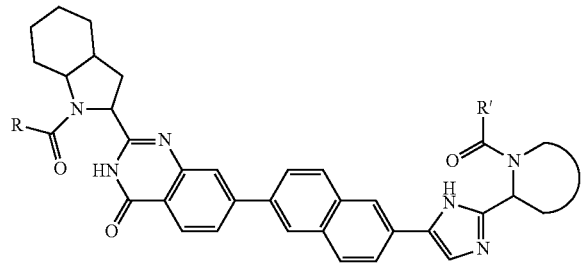

In a further embodiment of the invention, R$_2$ selected from the group comprising C$_{1-4}$alkylcarbonylamino or C$_{1-4}$alkyloxycarbonylamino.

In yet another embodiment of the invention, R$_1$ is selected from branched C$_{3-4}$alkyl; C$_{2-3}$alkyl substituted with methoxy; and phenyl optionally substituted with 1 substituent selected from halo and methyl.

In yet another embodiment of the invention, R$_3$ is hydrogen.

In a further embodiment R and R' are identical.

In yet a further embodiment R$_2$ is C$_{1-4}$alkylcarbonylamino or C$_{1-4}$alkyloxycarbonylamino, and R$^3$ is hydrogen.

The invention also provides a method for the treatment or prophylaxis of HCV infection, in particular of the genotype 1a or 1b, comprising administering to a subject in need thereof, a therapeutically effective amount of a compound as defined hereinbefore.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms or stereoisomers of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphorsulfonic acid. Alternatively, enantiomers may be separated by chromatographic techniques using chiral stationary phases. Said pure stereochemically isomeric forms may also be derived from the corresponding pure stereoisomeric forms of the appropriate starting materials, provided that the reaction occurs stereospecifically. Preferably, if a specific stereoisomer is desired, said compound is synthesized by stereospecific methods of preparation. These methods will advantageously employ enantiomerically pure starting materials.

The diastereomeric racemates of the compounds of formula I can be obtained separately by conventional methods. Appropriate physical separation methods that may advantageously be employed are, for example, selective crystallization and chromatography, e.g. column chromatography or supercritical fluid chromatography.

The compounds of formula I and subgroups of compounds of formula I as defined hereinbefore have several centers of chirality. Of interest are the stereogenic centers of the pyrrolidine ring at the 2-carbon atom. The configuration at this position may be that corresponding to L-proline, i.e.

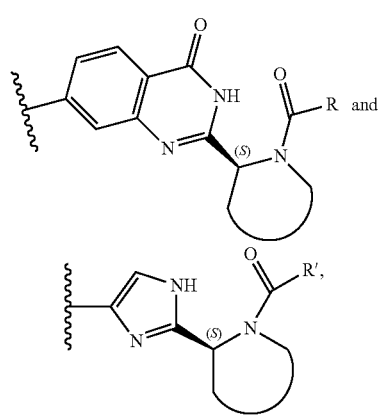

or that corresponding to D-proline, i.e.

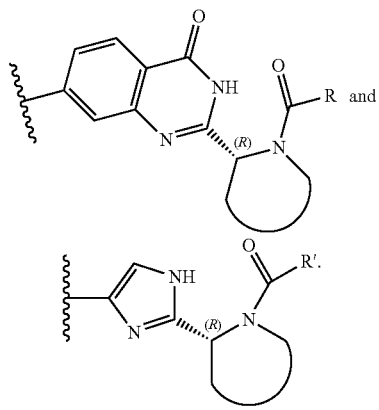

Of particular interest are compounds of formula I or subgroups thereof as defined herein, that are according to formula Ia.

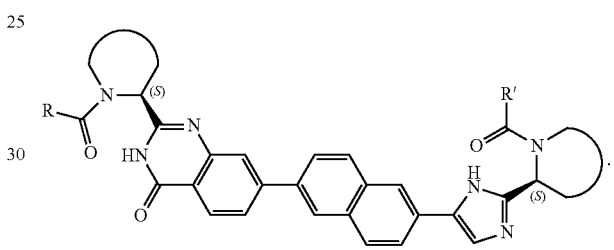

Also of interest is the configuration of the group —CR$_1$R$_2$R$_3$ wherein R$_3$ is H: when R$_1$ is selected from branched C$_{3-4}$alkyl; C$_{2-3}$alkyl substituted with methoxy, then the S-configuration is preferred; when R$_1$ is selected from phenyl optionally substituted with 1 or 2 substituents independently selected from halo and methyl; then the R-configuration is preferred.

The pharmaceutically acceptable addition salts comprise the therapeutically active non-toxic acid and base addition salt forms of the compounds of formula (I) or subgroups thereof. Of interest are the free, i.e. non-salt forms of the compounds of formula I, or of any subgroup of compounds of formula I specified herein.

The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propionic, hydroxyacetic, lactic, pyruvic, oxalic (i.e. ethanedioic), malonic, succinic (i.e. butanedioic acid), maleic, fumaric, malic (i.e. hydroxyl-butanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of formula (I) containing an acidic proton may also be converted into their base addition salts, in particular metal or amine addition salt forms, by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "solvates" covers any pharmaceutically acceptable solvates that the compounds of formula I as well as the salts thereof, are able to form. Such solvates are for example hydrates, alcoholates, e.g. ethanolates, propanolates, and the like.

Some of the compounds of formula I may also exist in tautomeric forms. For example, tautomeric forms of amide (—C(=O)—NH—) groups are iminoalcohols (—C(OH)=N—). Tautomeric forms, although not explicitly indicated in the structural formulae represented herein, are intended to be included within the scope of the present invention.

As used herein, "$C_{1-4}$alkyl" as a group or part of a group defines saturated straight or branched chain hydrocarbon groups having from 1 to 4 carbon atoms such as for example methyl, ethyl, 1-propyl, 2-propyl, 1-butyl, 2-butyl, 2-methyl-1-propyl, 2-methyl-2-propyl. For the purpose of the present invention, of interest amongst $C_{1-4}$alkyl is $C_{3-4}$alkyl, i.e. straight or branched chain hydrocarbon groups having 3 or 4 carbon atoms such as 1-propyl, 2-propyl, 1-butyl, 2-butyl, 2-methyl-1-propyl, 2-methyl-2-propyl. Of particular interest may be branched $C_{3-4}$alkyl such as 2-propyl, 2-butyl, 2-methyl-1-propyl, 2-methyl-2-propyl.

The term "$C_{3-6}$cycloalkyl" as a group or part thereof, defines saturated cyclic hydrocarbon groups having from 3 to 6 carbon atoms that together form a cyclic structure. Examples of $C_{3-6}$cycloalkyl include cyclopropyl, cyclobutyl, cyclopentyl and cyclohexyl.

"$C_{1-4}$alkoxy" as a group or part of a group means a group of formula —O—$C_{1-4}$alkyl wherein $C_{1-4}$alkyl is as defined above. Examples of $C_{1-4}$alkoxy are methoxy, ethoxy, n-propoxy, isopropoxy.

The term "halo" is generic to fluoro, chloro, bromo and iodo.

As used herein, the term "(=O)" or "oxo" forms a carbonyl moiety when attached to a carbon atom. It should be noted that an atom can only be substituted with an oxo group when the valency of that atom so permits.

As used herein for the purpose of defining "aryl" as a group or part thereof means an aromatic ring structure optionally comprising one or two heteroatoms selected from N, O and S, in particular from N and O. Said aromatic ring structure may have 5 or 6 ring atoms.

As used herein, the prefix "hetero-" in the definition of a group means that the group comprises at least 1 heteroatom selected from N, O and S, in particular N and O. For example, the term "heteroaryl" means an aromatic ring structure as defined for the term "aryl" comprising at least 1 heteroatom selected from N, O and S, in particular from N and O, for example furanyl, oxazolyl, pyridinyl. Alternatively, the term "hetero$C_{3-6}$cycloalkyl" means saturated cyclic hydrocarbon group as defined for "$C_{3-6}$cycloalkyl" further comprising at least 1 heteroatom selected from N, O and S, in particular from N and O, for example tetrahydrofuranyl, tetrahydropyranyl, piperidinyl.

Where the position of a group on a molecular moiety is not specified (for example a substituent on phenyl) or is represented by a floating bond, such group may be positioned on any atom of such a moiety, as long as the resulting structure is chemically stable. When any variable is present more than once in the molecule, each definition is independent.

Whenever used herein, the term "compounds of formula I", or "the present compounds" or similar terms, it is meant to include the compounds of formula I, including the possible stereoisomeric forms, and the pharmaceutically acceptable salts and solvates thereof.

General Synthetic Methods

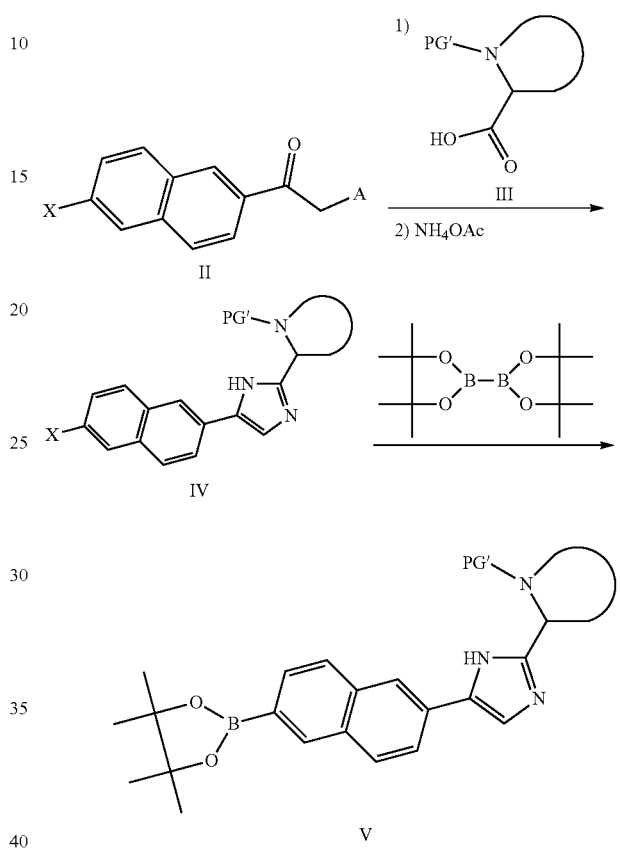

Scheme 1

Building blocks used in the synthesis of compounds of formula I are described in scheme 1. α-Amino ketone IIa (Scheme 1, A=NH$_2$), with X a halogen, in particular bromo or iodo, is coupled with a suitably protected derivative III, wherein PG' is a protective group on the nitrogen, preferably tert-butoxycarbonyl, in the presence of a coupling reagent for amino-group acylation, preferably HATU, in the presence of a base such as DIPEA. The thus formed intermediate is cyclized to an imidazole compound of general formula IV by treatment with ammonium acetate, preferably at a temperature ranging between 0° C. and 150° C.

Alternatively, the intermediate imidazole IV can be obtained by coupling an α-halo ketone IIb wherein X and A each independently represent a halo atom, X preferably selected from iodo or bromo and A preferably selected from chloro, bromo or iodo, with a suitably protected compound III wherein PG' is a protective group on the nitrogen, preferably tert-butoxycarbonyl, in the presence of a suitable base, for example DIPEA, followed by cyclization to the imidazole intermediate IV as described above. This intermediate IV can be transformed to a boronic ester of formula V under Pd catalyzed conditions, for example in the presence of Pd(dppf)Cl$_2$, bis(pinacolato)-diboron and a base, for example potassium acetate.

Other building blocks are described in scheme 2 (a, b).

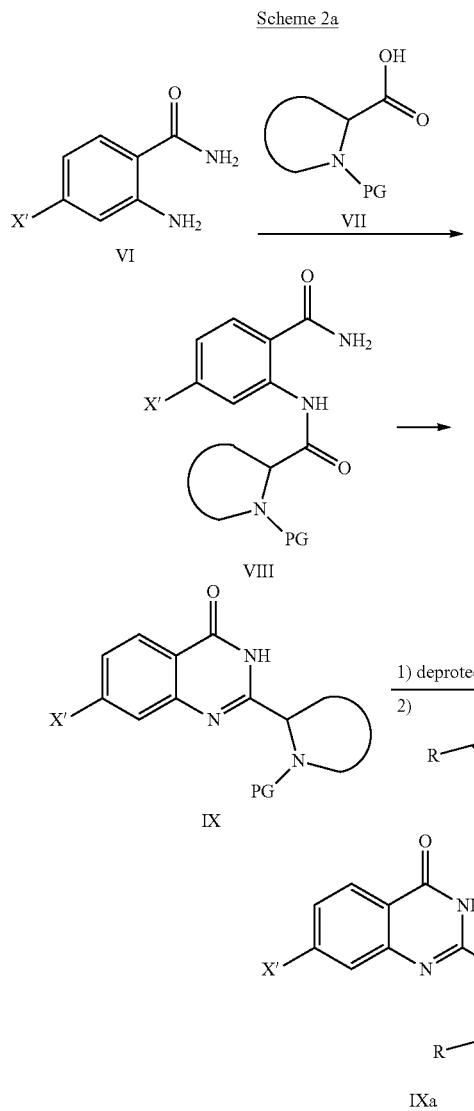

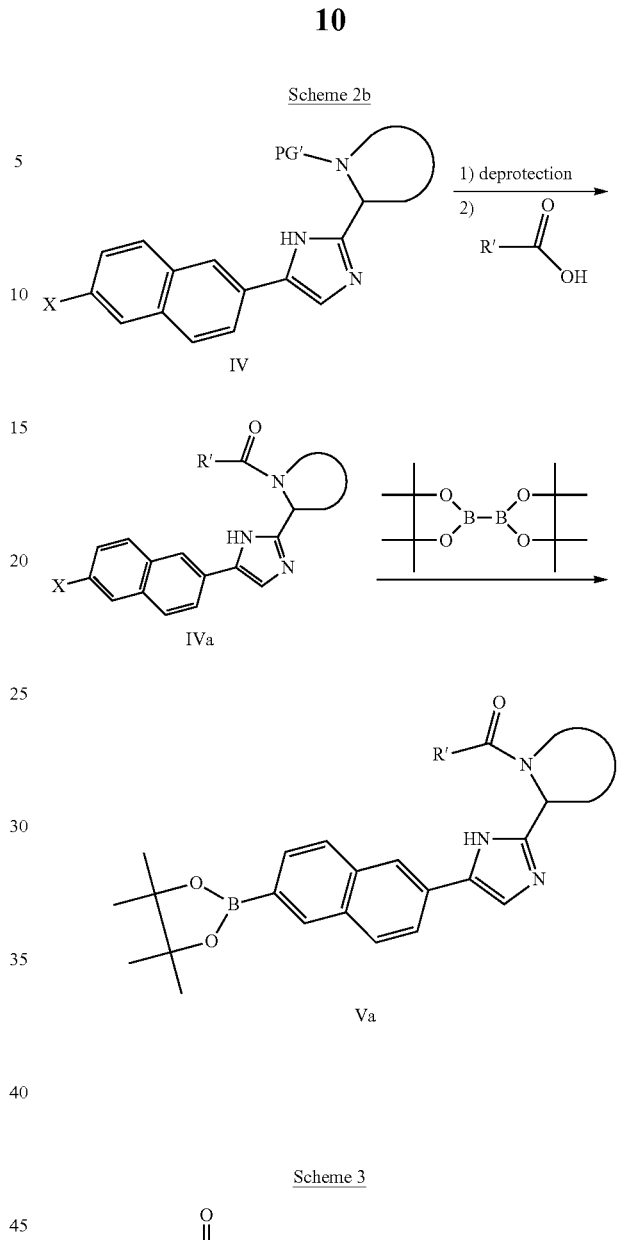

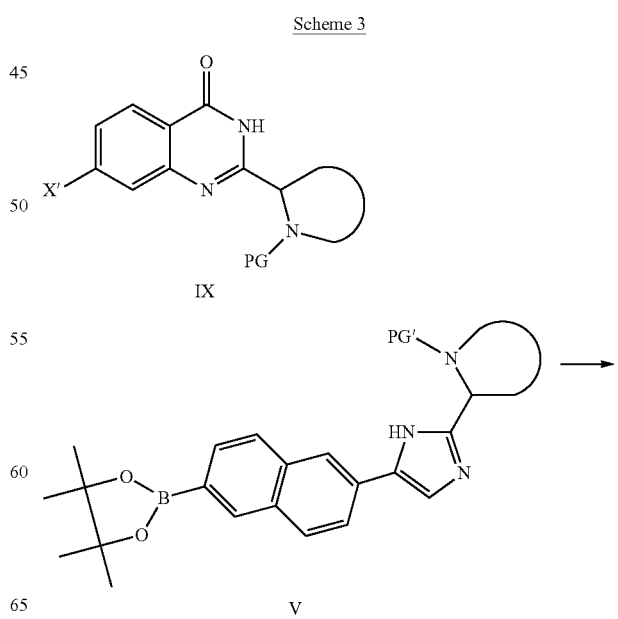

The synthesis of compounds of the formula IX and IXa is described in Scheme 2a. Amide bond formation starting from VI (X' is a halogen selected from iodo or bromo, preferably bromo) and VII results in the formation of compound VIII. This reaction can be effected by converting compound VII to an acid halogenide, for example an acid fluoride or acid chloride followed by reaction with VI in the presence of a base. Another example is the formation of VIII from VI and VII by use of the coupling reagent 4-(4,6-Dimethoxy[1.3.5] triazin-2-yl)-4-methylmorpholinium chloride or $BF_4$ (DMTMM). Compounds VIII are then converted to compounds of the general formula IX under basic conditions, for example KOH or $Na_2CO_3$ in ethanol. In case compounds of formula IX can be deprotected (fe HCl in dioxane in case PG equals tert-butyloxycarbonyl) the formed amine can be coupled with an acid of formula R(CO)OH under typical amide bond formation conditions (fe by treatment with HATU and a base like DIPEA or EDCI/HOBt/DIPEA)

Similarly, compounds of formula IV may be transformed to compounds of formula IVa and Va as depicted in scheme 2b.

-continued

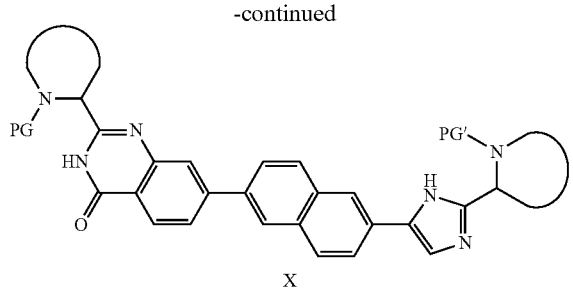

X

The building block IX, obtained by methods as described in scheme 2a and V (Scheme 1, 2b). can be converted to structure X, using Suzuki-Miyaura conditions (scheme 3).

Scheme 4

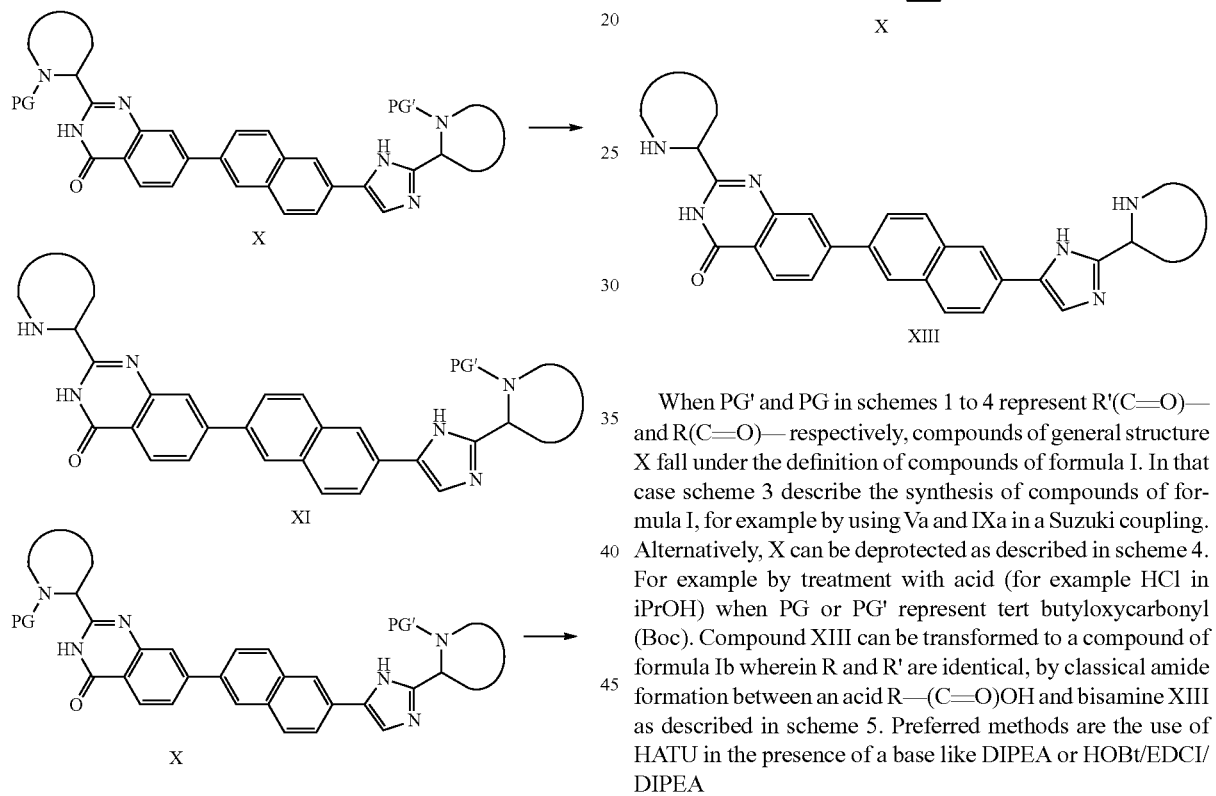

-continued

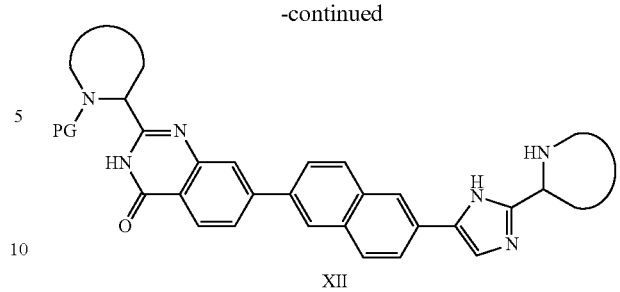

XII

When PG' and PG in schemes 1 to 4 represent R'(C=O)— and R(C=O)— respectively, compounds of general structure X fall under the definition of compounds of formula I. In that case scheme 3 describe the synthesis of compounds of formula I, for example by using Va and IXa in a Suzuki coupling. Alternatively, X can be deprotected as described in scheme 4. For example by treatment with acid (for example HCl in iPrOH) when PG or PG' represent tert butyloxycarbonyl (Boc). Compound XIII can be transformed to a compound of formula Ib wherein R and R' are identical, by classical amide formation between an acid R—(C=O)OH and bisamine XIII as described in scheme 5. Preferred methods are the use of HATU in the presence of a base like DIPEA or HOBt/EDCI/DIPEA Scheme 5

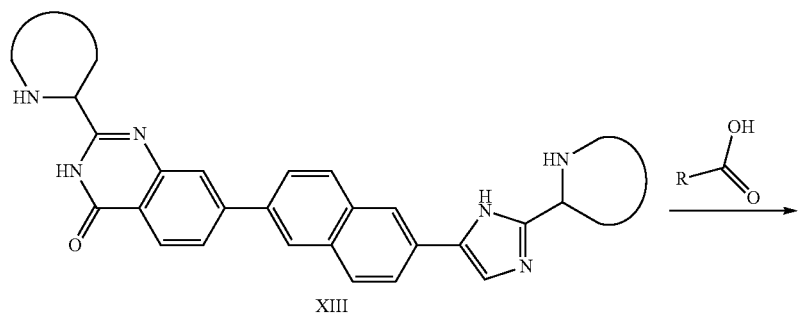

XIII

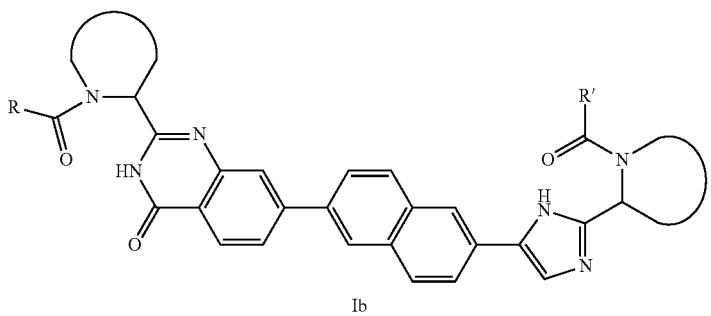

Ib

Where PG' differs from PG, selective deprotection is possible, as described in scheme 4, resulting in compounds XII or XI starting from X. For example in case PG' equals tert-butyloxycarbonyl (Boc) and PG equals benzyloxycarbonyl (Cbz), selective deprotection can be effected by removing the Boc-protective group under acidic conditions like HCl in iPrOH at room temperature, or by removing the CBz-protective group under reducing conditions like hydrogen in the presence of a catalyst, e.g. Pd(OH)$_2$.

When PG' represents R'(C=O)— or PG represents R(C=O)—, the synthesis of compounds X as described in scheme 1 to 3 results in compounds of formula XIV (Scheme 6) or XVI (Scheme 7) respectively. Compounds XIV and XVI can be obtained from compound XII and R'(C=O)OH or XI and R(C=O)OH respectively, under typical amide formation conditions. These compounds can then be transformed to compounds of formula I. Selective deprotection of XIV to XV followed by amide bond formation between XV and R(C=O)—OH results in compounds of the formula I. An analogous reaction sequence can then be applied to transform XVI into XVII and onwards to compounds of formula I.

Scheme 6

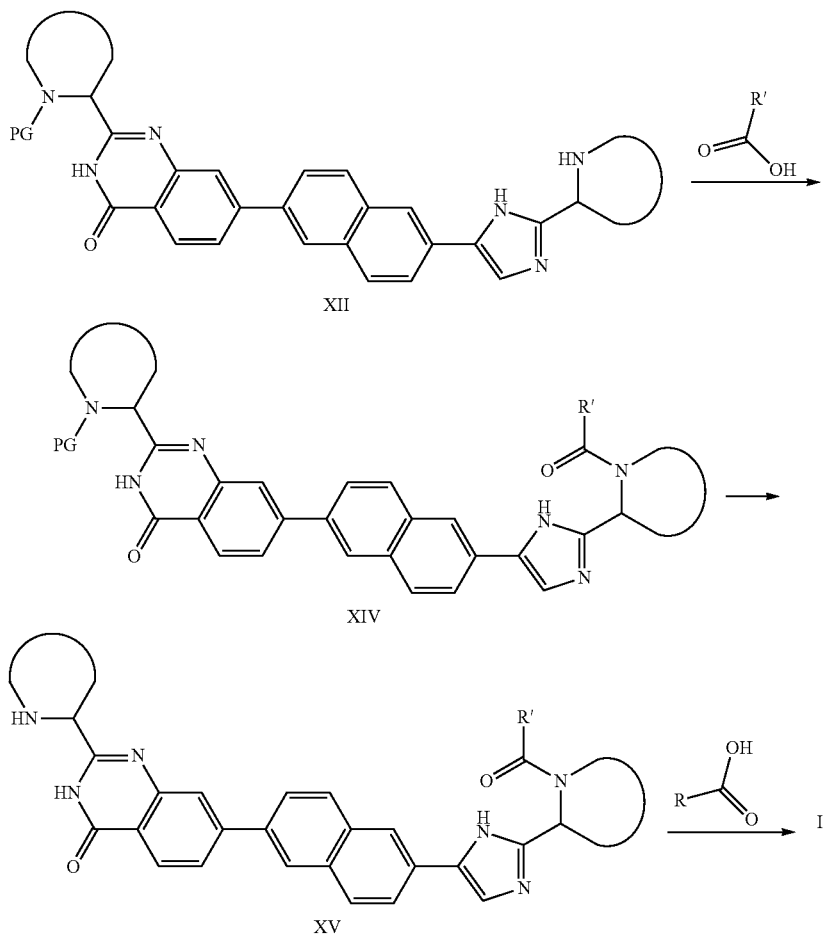

Scheme 7

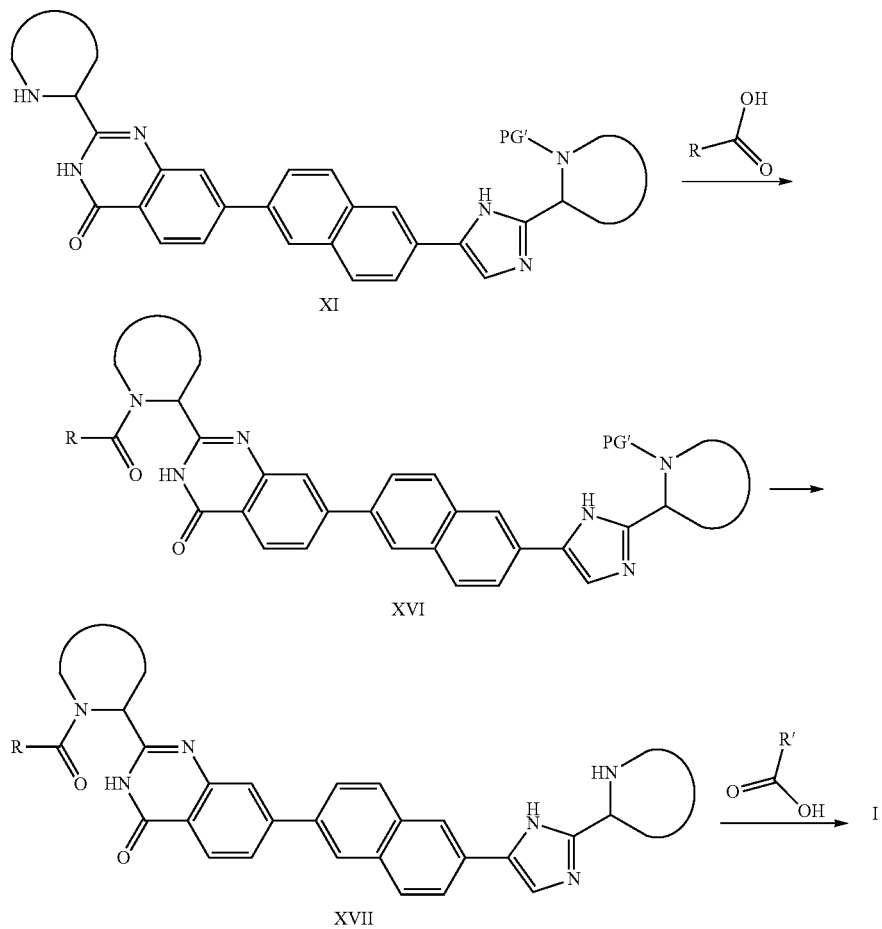

In a further aspect, the present invention concerns a pharmaceutical composition comprising a therapeutically effective amount of a compound of formula I as specified herein, and a pharmaceutically acceptable carrier. A therapeutically effective amount in this context is an amount sufficient to stabilize or to reduce HCV infection in infected subjects, or an amount sufficient to prevent HCV infection in subjects at risk of being infected. In still a further aspect, this invention relates to a process of preparing a pharmaceutical composition as specified herein, which comprises intimately mixing a pharmaceutically acceptable carrier with a therapeutically effective amount of a compound of formula I, as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof. The compounds of formula I show activity against HCV and can be used in the treatment and prophylaxis of HCV infection or diseases associated with HCV. The latter include progressive liver fibrosis, inflammation and necrosis leading to cirrhosis, end-stage liver disease, and hepatocellular carcinoma. A number of the compounds of this invention moreover are known to be active against mutated strains of HCV. Additionally, compounds of this invention may have attractive properties in terms of bioavailability, show a favorable pharmacokinetic profile, including an acceptable half-life, AUC (area under the curve), peak and trough values, and lack unfavorable phenomena such as insufficiently rapid onset or tissue retention.

The in vitro antiviral activity against HCV of the compounds of formula I can be tested in a cellular HCV replicon system based on Lohmann et al. (1999) Science 285:110-113, with the further modifications described by Krieger et al. (2001) Journal of Virology 75: 4614-4624 and Lohmann et al. (2003) Journal of Virology 77: 3007-3019 for genotype 1b and by Yi et al. (2004) Journal of Virology 78: 7904-7915 for genotype 1a (incorporated herein by reference), which is further exemplified in the examples section. This model, while not a complete infection model for HCV, is widely accepted as the most robust and efficient model of autonomous HCV RNA replication currently available. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

Due to their anti-HCV properties, the compounds of formula I or subgroups thereof, as specified herein, are useful in the inhibition of HCV replication, in particular in the treatment of warm-blooded animals, in particular humans, infected with HCV, and for the prophylaxis of HCV infections in warm-blooded animals, in particular humans. The present invention furthermore relates to a method of treating a warm-blooded animal, in particular a human, infected by HCV, or being at risk of infection by HCV, said method comprising the administration of a therapeutically or prophylactively effective amount of a compound of formula I, as defined hereinbefore.

The compounds of formula I as specified herein may therefore be used as a medicine, in particular as an anti-HCV medicine. Said use as a medicine or method of treatment comprises the systemic administration to HCV infected subjects or to subjects susceptible to HCV infection of an amount effective to relieve or prevent the symptoms and conditions associated with HCV infection.

The present invention also relates to the use of the present compounds in the manufacture of a medicament for the treatment or the prevention of HCV infection.

In general it is contemplated that an effective antiviral daily amount would be from about 0.01 to about 50 mg/kg, or about 0.02 to about 30 mg/kg body weight. It may be appropriate to administer the required dose as two, three, four or more sub-doses at appropriate intervals throughout the day. Said sub-doses may be formulated as unit dosage forms, for example, containing about 1 to about 500 mg, or about 1 to about 300 mg, or about 1 to about 100 mg, or about 2 to about 50 mg of active ingredient per unit dosage form.

Combination Therapy

The invention also relates to a combination of a compound of formula I, a pharmaceutically acceptable salt or solvate thereof, and another antiviral compound, in particular another anti-HCV compound. The term "combination" relates to a product containing (a) a compound of formula I, as defined hereinbefore, and (b) another anti-HCV inhibitor, as a combined preparation for simultaneous, separate or sequential use in the treatment of HCV infections.

The combinations of the present invention may be used as medicaments. Accordingly, the present invention relates to the use of a compound of formula (I) or any subgroup thereof as defined above for the manufacture of a medicament useful for inhibiting HCV activity in a mammal infected with HCV viruses, wherein said medicament is used in a combination therapy, said combination therapy in particular comprising a compound of formula (I) and at least one other anti-HCV agent, e.g. IFN-α, pegylated IFN-α, ribavirin, albuferon, taribavirin, nitazoxanide Debio025 or a combination thereof.

Other agents that may be combined with the compounds of the present invention include, for example, nucleoside and non-nucleoside inhibitors of the HCV polymerase, protease inhibitors, helicase inhibitors, NS4B inhibitors and agents that functionally inhibit the internal ribosomal entry site (IRES) and other agents that inhibit HCV cell attachment or virus entry, HCV RNA translation, HCV RNA transcription, replication or HCV maturation, assembly or virus release. Specific compounds in these classes include HCV protease inhibitors such as telaprevir (VX-950), boceprevir (SCH-503034), narlaprevir (SCH-900518), ITMN-191 (R-7227), TMC-435350 (TMC-435), MK-7009, BI-201335, BI-2061 (ciluprevir), BMS-650032, ACH-1625, ACH-1095, GS 9256, VX-985, IDX-375, VX-500, VX-813, PHX-1766, PHX2054, IDX-136, IDX-316, ABT-450, EP-013420 (and congeners) and VBY-376; the nucleoside HCV polymerase inhibitors useful in the invention include TMC649128, R7128, PSI-7851, PSI 7977, INX-189, IDX-184, IDX-102, R1479, UNX-08189, PSI-6130, PSI-938 and PSI-879 and various other nucleoside and nucleotide analogs and HCV inhibitors including those derived as 2'-C-methyl modified nucleosides, 4'-aza modified nucleosides, and 7'-deaza modified nucleosides. Non-nucleoside HCV polymerase inhibitors useful in the invention include HCV-796, HCV-371, VCH-759, VCH-916, VCH-222, ANA-598, MK-3281, ABT-333, ABT-072, PF-00868554, BI-207127, GS-9190, A-837093, JKT-109, GL-59728, GL-60667, ABT-072, AZD-2795 and TMC647055.

The following examples are meant to illustrate the invention and should not be construed as a limitation of its scope.

Experimental Part:

LCMS Methods

Method A: General: mobile phase A: H$_2$O (0.1% TFA; B:CH$_3$CN (0.05% TFA) Stop Time: 2 min; gradient time (min) [% A/% B] 0.01 [90/10] to 0.9 [20/80] to 1.5 [20/80] to 1.51 [90/10]; flow: 1.2 mL/min; column temp.: 50° C.

Method A1: Shimadzu LCMS 2010, Shim-pack XR-ODS, 3*30 mm

Method A2: Xtimate C18 2.1*30 mm, 3 um

Method A3: SHIMADZU Shim pack 2*30

Method B: Agilent 1100, YMC-PACK ODS-AQ, 50×2.0 mm 5 μm mobile phase A: H$_2$O (0.1% TFA; B:CH$_3$CN (0.05% TFA Stop Time: 10 min; gradient time(min) [% A/% B] 0 [100/0] to 1 [100/0] to 5 [40/60] to 7.5 [40/60] to 8 [100/0]; flow: 0.8 mL/min; column temp.: 50° C.

Method C: Agilent 1100, YMC-PACK ODS-AQ, 50×2.0 mm 5 μm mobile phase A: H$_2$O (0.1% TFA; B:CH$_3$CN (0.05% TFA); Stop Time: 10 min; gradient time(min) [% A/% B] 0 [90/10] to 0.8 [90/10] to 4.5 [20/80] to 7.5 [20/80] to 8 [90/10]; flow: 0.8 mL/min; column temp.: 50° C.

Method D: Shimadzu LCMS 2010, Shim-pack XR-ODS, 3*30 mm, mobile phase A: H$_2$O (0.1% TFA; B:CH$_3$CN (0.05% TFA) Stop Time: 2 min; gradient time (min) [% A/% B] 0.01 [100/0] to 0.9 [70/30] to 1.5 [70/30] to 1.51 [100/0]; flow: 1.2 mL/min; column temp.: 50° C.

Method E: Liquid Chromatography: Waters Alliance 2695, UV detector:Waters 996 PDA, range:210-400 nm; Mass detector: Waters ZQ, ion source: ES+, ES− Column used: SunFire C18 3.5 g 4.6×100 mm mobile phase A: 10 mM NH$_4$OOCH+0.1% HCOOH in H$_2$O; mobile phase B: CH$_3$OH; column temp.: 50° C.; flow: 1.5 mL/min. gradient time (min) [% A/% B] 0 [65/35] to 7 [5/95] to 9.6 [5/95] to 9.8 [65/35] to 12 [65/35].

Method F: Xtimate C18 2.1*30 mm, 3 um, mobile phase A: H$_2$O (1.5 mL TFA/4 L); B:CH$_3$CN (0.75 mL TFA/4 L) Stop Time: 3 min; gradient time(min) [% A/% B] 0.0 [90/10] to 1.35 [20/80] to 2.25 [20/80] to 2.26 [90/10]; 3.0 [90/10] flow: 0.8 mL/min; column temp.: 50° C.

Method G: General conditions: mobile phase A: H$_2$O (1.5 mL TFA/4 L); B:CH$_3$CN (0.75 mL TFA/4 L) Stop Time: 2 min; gradient time(min) [% A/% B] 0.0 [100/0] to 0.9 [40/60] to 1.5 [40/60] to 1.51 [100/0]; 2.0 [100/0] flow: 1.2 mL/min; column temp.: 50° C.

Method G1: Xtimate C18, 2.1*30 mm, 3 um

Method H: General conditions: mobile phase A: H$_2$O (0.1% TFA); B:CH$_3$CN (0.05% TFA) Stop Time: 10 min; gradient time(min) [% A/% B] 0.0 [90/10] to 0.8 [90/10] to 4.5 [20/80] to 7.5 [20/80]; 9.5 [90/10] flow: 0.8 mL/min; column temp.: 50° C.

Method H1: Agilent TC-C18, 2.1*50 mm, 5 um

Method I: Shimadzu LCMS 2010, Shim-pack XR-ODS, 3*30 mm, mobile phase A: H$_2$O (0.1% TFA; B:CH$_3$CN (0.05% TFA) Stop Time: 7 min; gradient time(min) [% A/% B]0.01 [90/10] to 6.0 [20/80] to 6.5 [20/80] to 6.51 [90/10]; flow: 0.8 mL/min; column temp.: 50° C.

Method J: Agilent TC-C18, 50×2.1 mm, 5 μm, mobile phase A: H$_2$O (0.1% TFA; B:CH$_3$CN (0.05% TFA) Stop Time: 10 min; Post Time: 0.5 min; gradient time(min) [% A/% B]0 [100/0] to 1 [100/0] to 5 [40/60] to 7.5 [15/85] to 9.5 [100/0]; flow: 0.8 mL/min; column temp.: 50° C.

Synthesis of Intermediates:

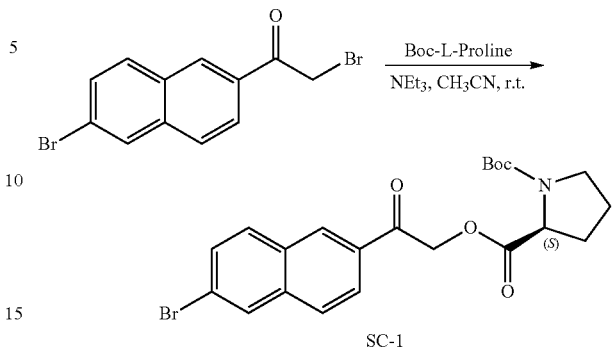

2-Bromo-1-(6-bromonaphthalen-2-yl)ethanone (526.5 g, 1204 mmol) was dissolved in CH$_3$CN (6000 mL). Boc-L-proline (284 g, 1325 mmol) was added to the solution and the reaction mixture was stirred for 20 minutes at room temperature. Et$_3$N (480 mL, 3612 mmol) was added dropwise to the solution. The reaction mixture was stirred for 15 hours at room temperature. The solvent was removed in vacuo and crude SC-1 (794 g) was used in the next step without further purification. Method A1; Rt: 1.68 min. m/z: 484.1 (M+Na)$^+$ Exact mass: 461.1

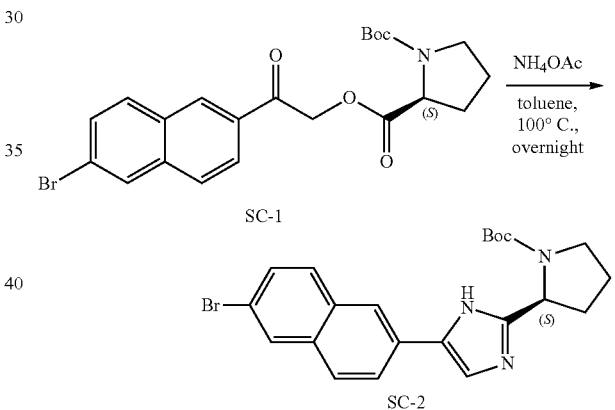

SC-1 (794 g, 1204 mmol) was dissolved in toluene (6000 mL) and ammonium acetate (1855 g, 24096 mmol) was added to the solution. The mixture was stirred for 12 hours at 100° C. The solution was diluted with ethyl acetate (1000 mL), and washed with water (2×500 mL). The inorganic layer was extracted with ethyl acetate (2×500 mL). The combined organic layers were concentrated in vacuo. The residue was triturated in CH$_3$CN (300 mL) for 0.5 hours at 0° C., resulting in compound SC-2 (140 g, 26% yield based on 1-(6-bromonaphthalen-2-yl)ethanone). Method A; Rt: 1.28 min. m/z: 442.1 (M+H)$^+$ Exact mass: 441.1

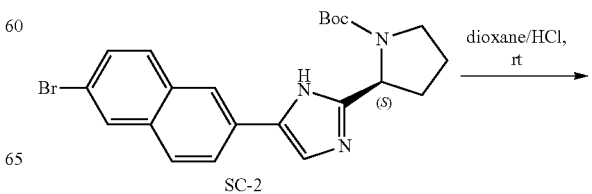

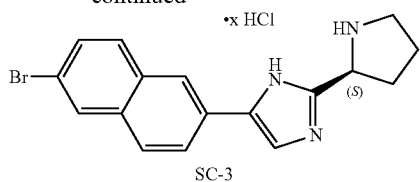

To the solution of compound SC-2 (75 g, 170 mmol) was added dioxane/HCl (750 mL) at room temperature and the mixture was stirred for 1 hour. The mixture was filtered to obtain compound SC-3 (73 g).

mmol) at room temperature. The mixture was stirred for 30 minutes at room temperature and SC-3 (73 g) was added. The solution was then cooled to 0° C., diisopropylethylamine (75 g, 578 mmol) was added and the mixture was stirred at room temperature overnight. The mixture was diluted with $CH_2Cl_2$ (1500 mL) and washed with NaOH aqueous (0.5 N, 1000 mL). The organic layer was washed with brine. The combined organic layer was dried and concentrated. The obtained crude product was washed with $CH_3CN$, resulting in compound SC-4 (80 g).

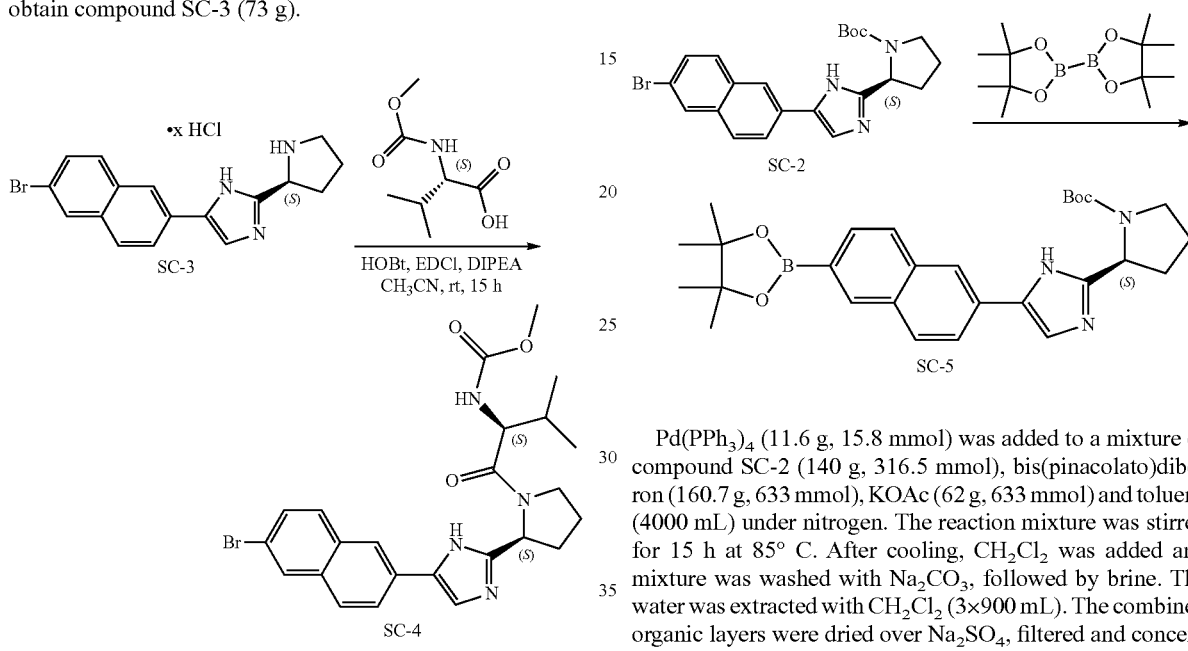

To a solution of (S)-2-(methoxycarbonylamino)-3-methylbutanoic acid (47.2 g, 270 mmol) in $CH_3CN$ (1200 mL) were added HOBt (36.4 g, 270 mmol) and EDCI (51.6 g, 270

$Pd(PPh_3)_4$ (11.6 g, 15.8 mmol) was added to a mixture of compound SC-2 (140 g, 316.5 mmol), bis(pinacolato)diboron (160.7 g, 633 mmol), KOAc (62 g, 633 mmol) and toluene (4000 mL) under nitrogen. The reaction mixture was stirred for 15 h at 85° C. After cooling, $CH_2Cl_2$ was added and mixture was washed with $Na_2CO_3$, followed by brine. The water was extracted with $CH_2Cl_2$ (3×900 mL). The combined organic layers were dried over $Na_2SO_4$, filtered and concentrated in vacuo. The residue was re-crystallized in a mixed solvent of hexane/i-$Pr_2O$ (3/2, 2×150 mL) resulting in compound SC-5 (105 g, 63% yield). Method A3; Rt: 1.35 min. m/z: 490.1 $(M+H)^+$ Exact mass: 489.3

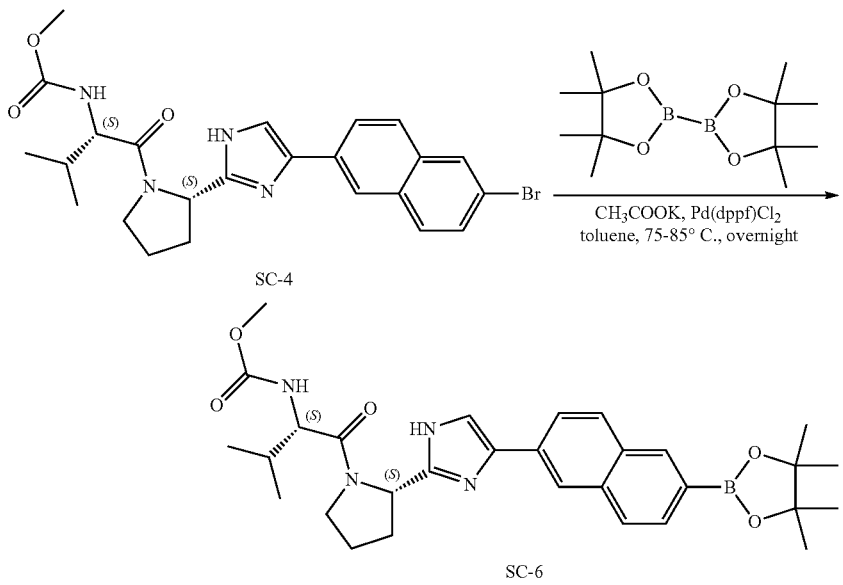

SC-4 (69 g, 138.2 mmol), 4,4,4',4',5,5,5',5'-octamethyl-2,2'-bi(1,3,2-dioxaborolane) (70.2 g, 276.4 mmol) and CH₃COOK (27.1 g, 276.4 mmol) were added to toluene (1500 mL) followed by Pd(dppf)Cl₂ (5 g, 6.9 mmol) under N₂ at room temperature. The reaction mixture was stirred at 80° C. overnight. After cooling, ethyl acetate (1000 mL) was added and the mixture was washed with saturated NaHCO₃ (1500 mL) and brine. The water layer was extracted with ethyl acetate. The organic layer were dried over Na₂SO₄ and after filtration, concentrated in vacuo. The crude product was purified by column chromatography resulting in compound SC-6 (52 g, 68% yield). Method C; Rt: 4.01 min. m/z: 547.3 (M+H)⁺ Exact mass: 546.3

SFC: Column: (AS)—H 150 mm×4.6 mm; 5 um. Flow: 3 mL/min, Mobile phase: A: CO₂ B: EtOH (0.05% Diethylamine); 5 to 40% B in A,: Rt: 3.11 min SFC: Column: OD-H 50 mm×4.6 mm; 3 um. Flow: 4 mL/min, Mobile phase: A: CO₂ B: EtOH (0.05% Diethylamine); 5 to 40% B in A,: Rt: 1.34 min

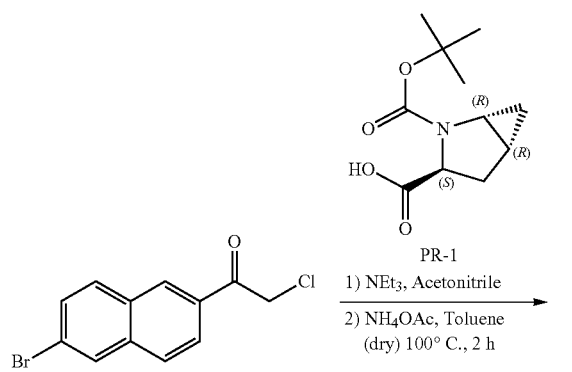

PR-1

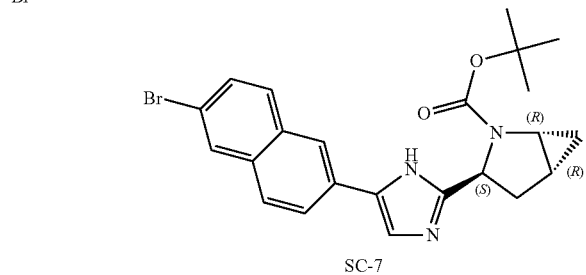

SC-7

1-(6-bromonaphthalen-2-yl)-2-chloroethanone (5.53 g, 18.79 mmol) was dissolved in acetonitrile (15 mL). PR-1 (4.27 g, 18.79 mmol) and NEt₃ (6.65 g, 65.76 mmol) were added at 25° C. and the mixture was stirred for 5 hours. The volatiles were removed in vacuo, resulting in a residue that was used as such. A solution of the obtained residue (10 g, 18.79 mmol) was dissolved in dry toluene (50 mL) and stirred at 20° C. NH₄OAc (29 g, 375.8 mmol) was added and the mixture was stirred for 2 hours at 100° C. The solution was diluted with ethyl acetate (50 mL) and washed with H₂O (40 mL). The organic layer was dried over Na₂SO₄ and after filtration, the volatiles were removed in vacuo. The obtained residue was purified by silic gel column chromatography (Gradient eluent: petroleum ether/ethyl acetate from 100/1 to 1/100). The pure fractions were collected and the solvent was removed in vacuo, resulting in compound SC-7 (6.5 g) Method A2; Rt: 0.94 min. m/z: 456.0 (M+H)⁺ Exact mass: 455.1

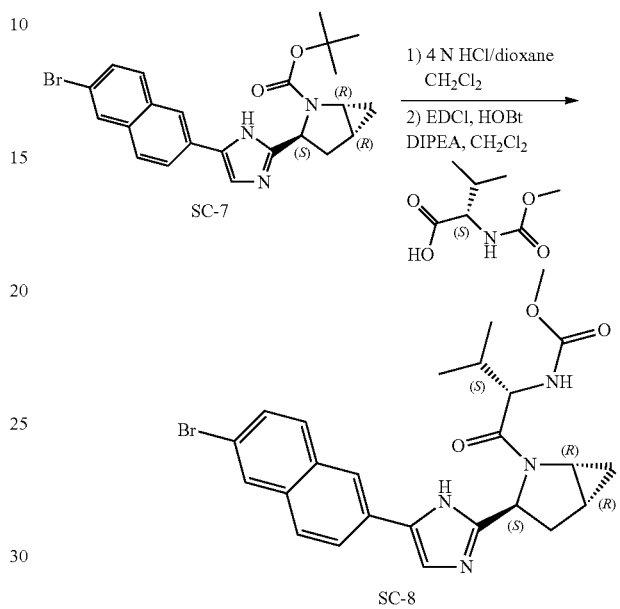

SC-8

Compound SC-7 (6.5 g, 14.3 mmol) was dissolved in CH₂Cl₂ (30 mL) and stirred at 20° C. 4 N HCl/dioxane (30 mL) was added dropwise at 0° C. The mixture was then stirred at 25° C. for 1 hour after which the volatiles were removed in vacuo, resulting in a residue (8 g). Method A2; Rt: 0.84 min. m/z: 353.9 (M+H)⁺ Exact mass: 353.1 This residue was used in the next step without further purification. A mixture of the obtained residue (8 g), (S)-2-(methoxycarbonylamino)-3-methylbutanoic acid (5.5 g, 31.5 mmol), EDCI (6.0 g, 31.5 mmol) and HOBt (4 mL, 31.5 mmol) in CH₂Cl₂ (80 mL) were stirred at 0° C. and DIPEA (18.48 g, 143 mmol) was added. The mixture was stirred at 20° C. for 12 hours. The mixture was diluted with CH₂Cl₂ (20 mL) and H₂O (50 mL). The organic layer was separated and washed with saturated aqueous NaHCO₃ (50 mL), brine and dried over Na₂SO₄. The volatiles were removed in vacuo and the resulting residue was purified by silica gel column chromatography (eluent: petroleum ether/ethyl acetate from 100/1 to 1/100). The pure fractions were collected and the solvent was removed in vacuo, resulting in compound SC-8 (4.6 g). Method A2; Rt: 1.00 min. m/z: 512.9 (M+H)⁺ Exact mass: 512.1

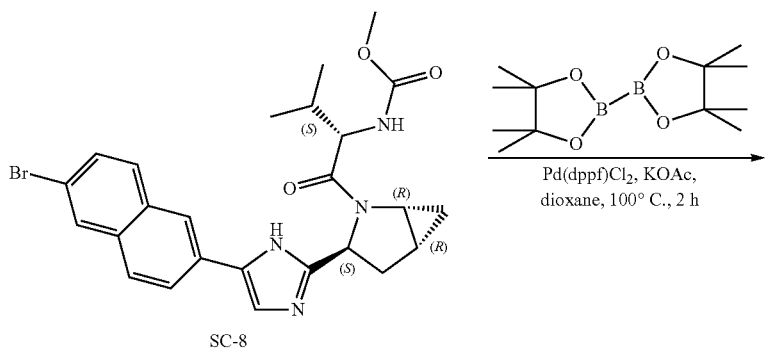

SC-8

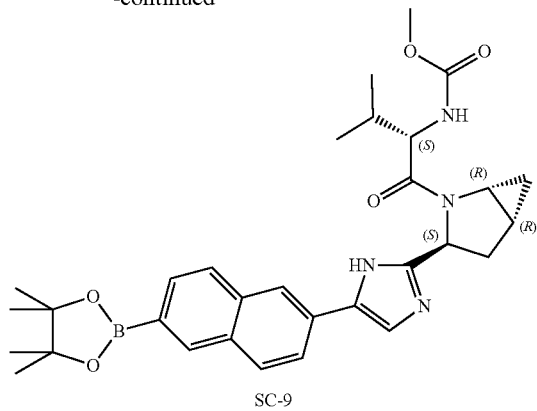

SC-9

A mixture of compound SC-8 (4.6 g, 8.99 mmol), 4,4,4',4',5,5,5',5'-octamethyl-2,2'-bi(1,3,2-dioxaborolane) (4.57 g, 17.99 mmol), Pd(dppf)Cl$_2$ (0.66 g, 0.9 mmol) and KOAc (1.76 g, 17.99 mmol) in dioxane (50 mL) were stirred for 2 hours at 100° C. under a N$_2$ atmospher. The mixture was filtered and the filtrate was concentrated in vacuo. The obtained residue was purified by silica gel column chromatography (gradient eluent: petroleum ether/ethyl acetate from 100/1 to 1/100). The fraction containing product were collected and the solvent was removed in vacuo, resulting in compound SC-9 (4.8 g). Method A2; Rt: 0.98 min. m/z: 559.3 (M+H)$^+$ Exact mass: 558.3

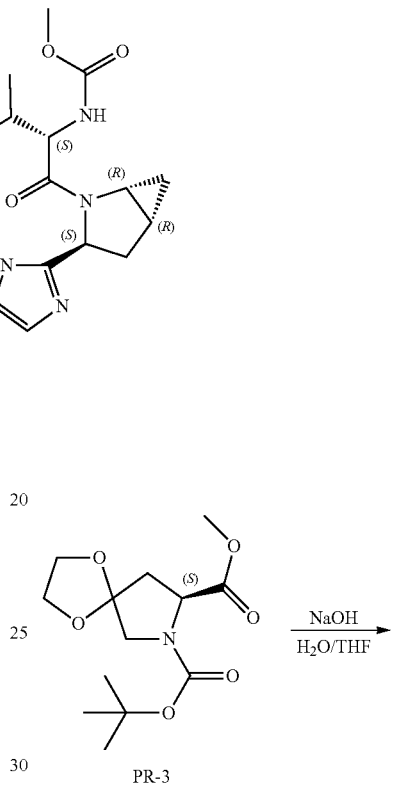

PR-3

PR-4

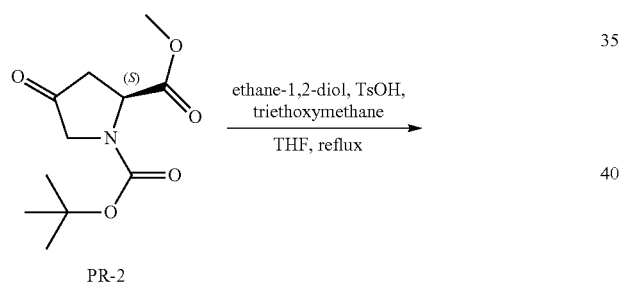

PR-2 → PR-3

To compound PR-2 (30 g, 123 mmol) in THF (120 mL), ethane-1,2-diol (53.6 g, 864 mmol), triethoxymethane (54.6 g, 369 mmol) and TsOH (3 g, 3.69 mmol) were added at 25° C. The mixture was stirred at refluxed for 5 hours. The mixture was poured into aqueous NH$_4$Cl (400 mL) and extracted with ethyl acetate (3×100 mL). The combined organic layers were washed with brine and dried over Na$_2$SO$_4$. The organic phase was concentrated in vacuo. The obtained residue was purified by silica gel column chromatography (hexane: ether acetate=10:1) resulting in compound PR-3 (8.4 g).

To a stirred solution of compound PR-3 (8.4 g, 29.3 mmol) in THF/H$_2$O (100 mL, 1:1) was added NaOH (5.85 g, 146 mmol). The reaction mixture was stirred at 20° C. for 1 hour and treated with ethyl acetate (20 mL). The combined inorganic layer was separated, adjusted to pH=4 with 2N HCl, and extracted with CH$_2$Cl$_2$ (3×50 mL). The combined organic layer was washed with brine, dried over Na$_2$SO$_4$ and concentrated in vacuo resulting in compound PR-4 (5.9 g).

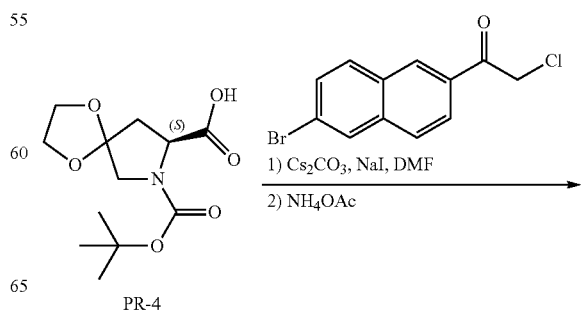

PR-4

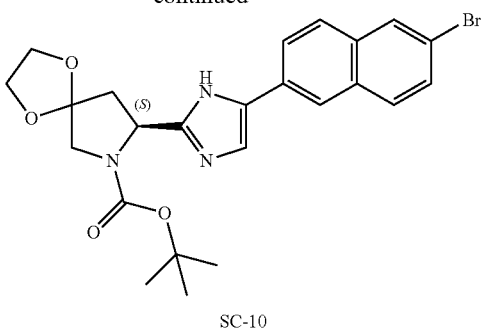

SC-10

To a stirred solution of compound PR-4 (5.9 g, 21.6 mmol) in DMF (100 mL) was added Cs$_2$CO$_3$ (10.6 g, 32.4 mmol), and the reaction mixture was stirred at 20° C. for 0.5 hour. Then 1-(6-bromonaphthalen-2-yl)-2-chloroethanone (9.2 g, 32.4 mmol) and NaI (4.86 g, 32.4 mmol) were added to the mixture and the stirring was continued at 20° C. for 2 hour. The mixture was washed with water (90 mL) and extracted with ethyl acetate (3×50 mL), the combined organic layers were washed with brine, dried over Na$_2$SO$_4$ and concentrated in vacuo. The residue was purified by column chromatography (hexane:ether acetate=5:1) resulting in a residue (5.9 g).

To a stirred solution of the obtained residue, obtained as described above, (8.4 g, 16.2 mmol) in xylene (80 mL) in an autoclave was added NH$_4$OAc (26.2 g, 32.3 mmol), and the reaction mixture was stirred at 160° C. for 1 hour. The mixture was cooled, washed with water (90 mL) and extracted with ethyl acetate (3×30 mL); the combined organic layer was washed with brine, dried over Na$_2$SO$_4$ and concentrated in vacuo. The residue was purified by column chromatography (hexane:ether acetate=2:1) resulting in compound SC-10 (5.2 g). Method A2; Rt: 1.07 min. m/z: 500.0 (M+H)$^+$ Exact mass: 499.1

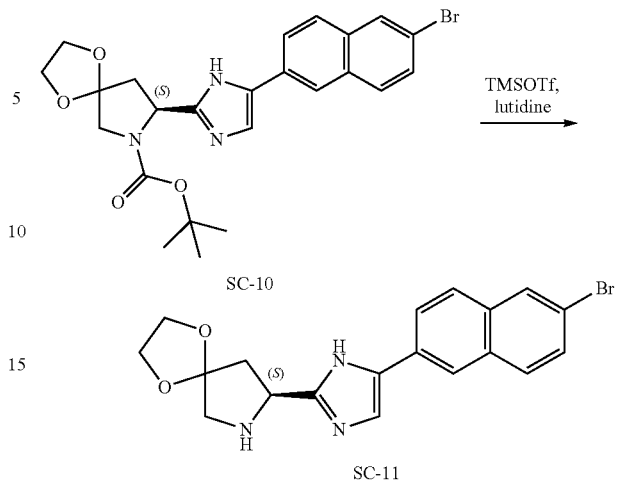

To a stirred solution of compound SC-10 (5.2 g, 10.4 mmol) and lutidine (2.2 g, 20.8 mmol) in dry CH$_2$Cl$_2$ (100 mL) at 0° C., TMSOTf (9.2 g, 40.6 mmol) was added drop wise. The reaction mixture was stirred at 0° C. for 30 minutes, quenched with saturated aqueous NH$_4$Cl, and extracted with ethyl acetate (3×50 mL); the combined organic layers were washed with brine, dried over Na$_2$SO$_4$ and concentrated in vacuo resulting in compound SC-11 (3.0 g) as off-white solid. Method A2; Rt: 0.98 min. m/z: 401.9 (M+H)$^+$ Exact mass: 401.1

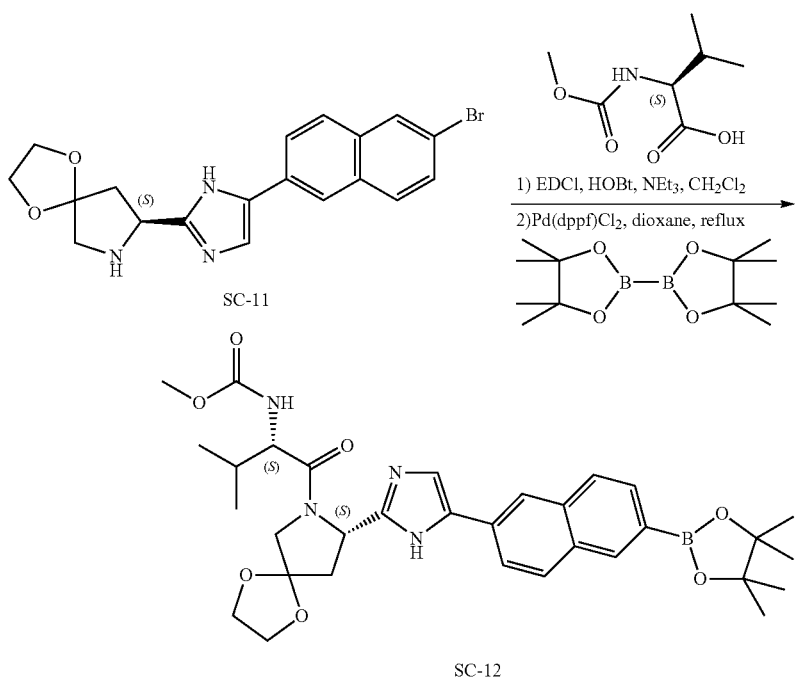

To a stirred solution of compound SC-11 (3.0 g), (S)-2-(methoxycarbonylamino)-3-methylbutanoic acid (1.57 g, 9 mmol), EDCI (1.73 g, 9 mmol) and HOBt (0.12 g, 0.9 mmol) in dry CH$_2$Cl$_2$ (50 mL) was added NEt$_3$ (15.2 g, 15 mmol). The reaction mixture was stirred at 20° C. for 2 hours, quenched with saturated aqueous Na$_2$CO$_3$, and extracted with CH$_2$Cl$_2$ (3×10 mL); the combined organic layer was washed with brine, dried over Na$_2$SO$_4$ and concentrated in vacuo. The residue was purified by silica gel column chromatography (hexane:ether acetate=1:1) resulting in a white solid residue (2.2 g). To a stirred solution of this residue (2.2 g) and Pd (dppf) Cl₂ (0.2 g, 0.395 mmol) in dry dioxane (25 mL) was added 4,4,4',4',5,5,5',5'-octamethyl-2,2'-bi(1,3,2-dioxaborolane) (1.5 g, 5.93 mmol) and KOAc (0.77 g, 7.9 mmol). The reaction mixture was stirred at reflux for 20 minutes, quenched with water, and extracted with ethyl acetate (3×20 mL). The combined organic layer was washed with brine, dried over Na₂SO₄ and concentrated in vacuo. The residue was purified by silica gel column chromatography (hexane: ether acetate=1:1) resulting in compound SC-12 (1.9 g) as a solid. Method A2; Rt: 0.97 min. m/z: 605.1 (M+H)⁺ Exact mass: 604.3

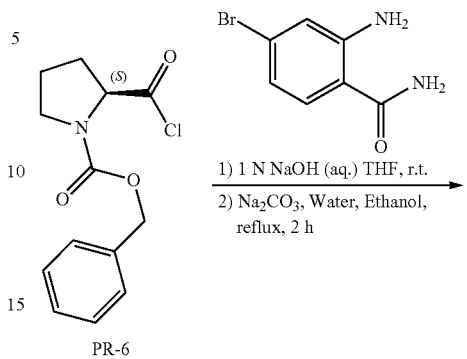

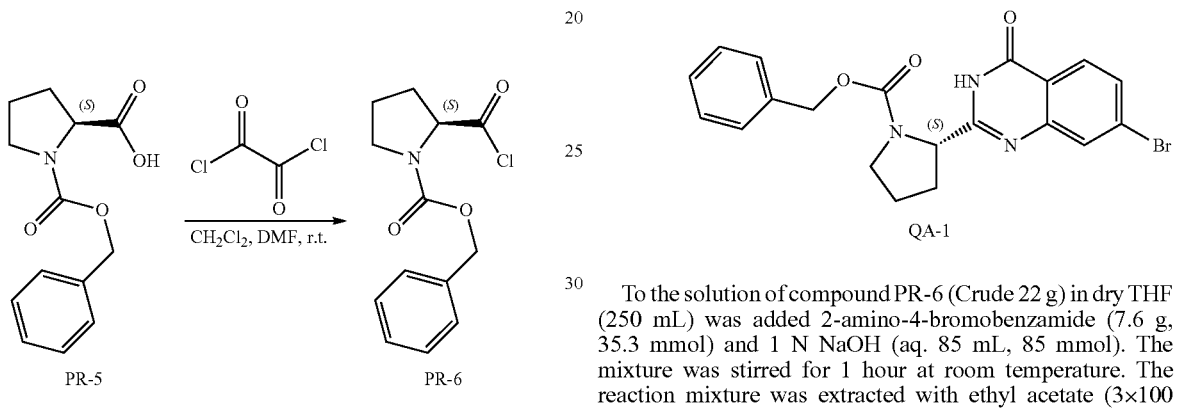

Compound PR-5 (15.7 g, 63.1 mmol) was dissolved in dry CH₂Cl₂ (250 mL) and DMF (1.5 mL) was added to the solution. Oxalyl chloride (13.5 mL, 157.5 mmol) was added drop wise at room temperature. The reaction mixture was stirred for 0.5 hour at room temperature. The reaction mixture was concentrated in vacuo and the residue (PR-6, 22 g) was used directly without further purification.

To the solution of compound PR-6 (Crude 22 g) in dry THF (250 mL) was added 2-amino-4-bromobenzamide (7.6 g, 35.3 mmol) and 1 N NaOH (aq. 85 mL, 85 mmol). The mixture was stirred for 1 hour at room temperature. The reaction mixture was extracted with ethyl acetate (3×100 mL). The combined organic layers were washed with 1 N NaOH in water (15 mL), brine, dried over Na₂SO₄ and concentrated in vacuo resulting in a crude residue (17 g). The crude residue, obtained similar as described above (25 g), and Na₂CO₃ (17.8 g, 168 mmol) in ethanol (250 mL) and H₂O (250 mL) was refluxed for 2 hour. The organic solvent was removed in vacuo. The mixture was extracted with dichloromethane (2×200 mL). The combined organic layers were washed with brine, dried over Na₂SO₄ and purified by silica gel column chromatography (eluent: ethyl acetate). The desired fractions were evaporated to dryness. The obtained residue was stirred in ethyl acetate (50 mL), the precipitate was filtered off and washed with ethyl acetate resulting in compound QA-1 (17 g).

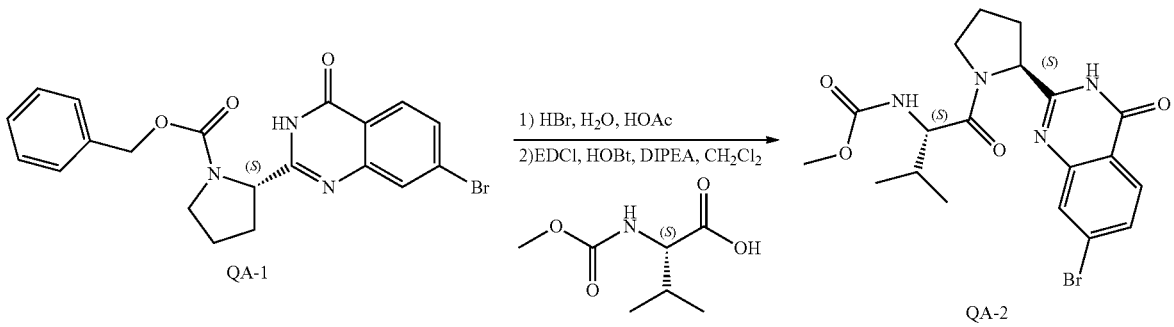

Compound QA-1 (8 g, 18.6 mmol) was dissolved in HOAc (80 mL) and 40% HBr (40 mL) was added. The mixture was stirred at 80° C. overnight. Most of the solvent was removed in vacuo. The precipitate was filtered off and washed with methyl t-butyl ether. The solid was co-evaporated with toluene (2×20 mL) resulting in a crude residue (6.5 g). Part of this residue (6.4 g), (S)-2-(methoxycarbonylamino)-3-methylbutanoic acid (4.5 g, 25.6 mmol), EDCI (4.9 g, 25.6 mmol) and HOBt (1.15 g, 8.5 mmol) in CH$_2$Cl$_2$ (120 mL) were then cooled to 0° C. DIPEA (14.8 mL, 85.0 mmol) was added. The mixture was stirred for 1.5 hour at 20° C. The organic layer was washed with saturated aqueous NaHCO$_3$ (100 mL) and dried over Na$_2$SO$_4$. The solvent was removed in vacuo. The residue was purified by silica gel column chromatography (gradient eluent: petroleum ether:ethyl acetate: from 100:0 to 0:100) resulting in compound QA-2 (3.3 g).

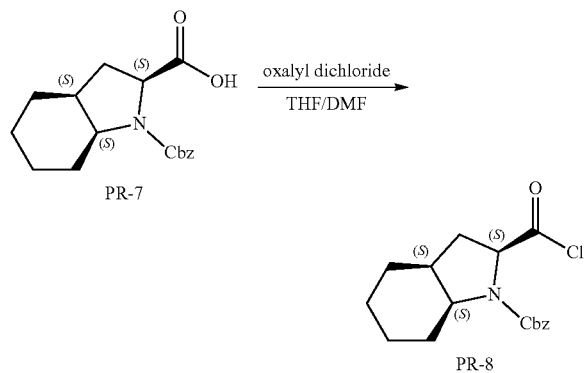

Compound PR-7 (7.0 g, 23.21 mmol) in THF (70 mL) was stirred at 0° C. Oxalyl dichloride (7 mL, 46.2 mmol) and DMF (2 drops) were added dropwise and the mixture was stirred for 10 min at 0° C. The mixture was stirred and refluxed for 1 hour. The mixture was cooled and evaporated in vacuo, resulting in compound PR-8 (7 g)

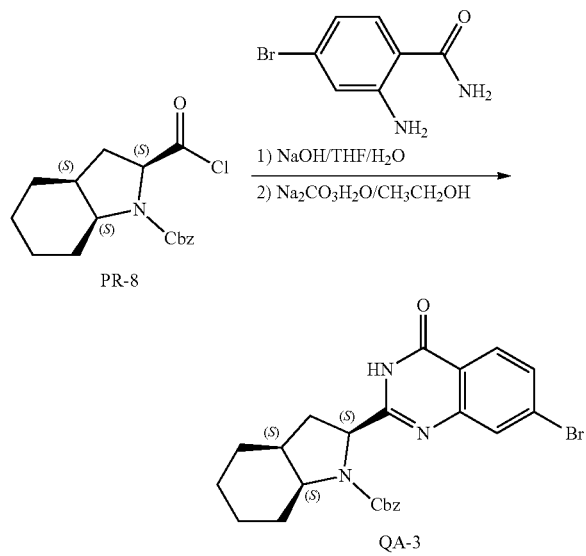

To the solution of compound PR-8 (7 g, 21 mmol) in THF (70 mL) was added 2-amino-4-bromobenzamide (4.5 g, 21 mmol) and 1N NaOH (42 mL, 42 mmol). The mixture was stirred for 1 hour at 25° C. The mixture was extracted with ethyl acetate. The organic layers were collected, washed with 0.5 N NaOH, brine, dried and concentrated in vacuo, resulting in a crude residue (9 g). This residue (9 g) and Na$_2$CO$_3$ (5.7 g, 54 mmol) in H$_2$O (200 mL) and THF (200 mL) was stirred and refluxed for 2 hour. The mixture was concentrated in vacuo and extracted with CH$_2$Cl$_2$ (2×), washed with brine, dried and evaporated in vacuo. The residue was dissolved in CH$_2$Cl$_2$ and washed with 1 N HCl (3×), brine, dried and evaporated in vacuo, resulting in QA-3 (4.4 g). Method A2; Rt: 1.27 min. m/z=: 484.0 (M+H)$^+$ Exact mass: 483.1

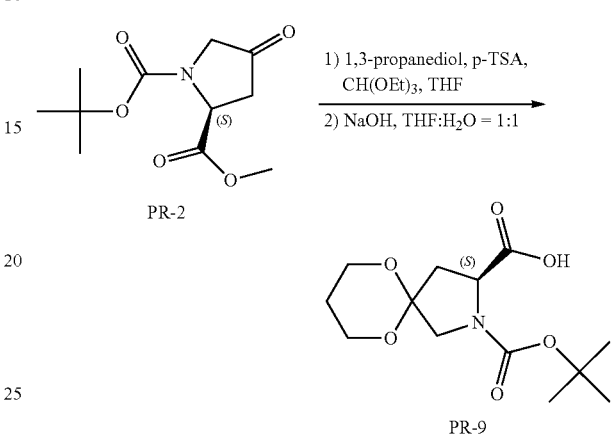

To compound PR-2 (10 g, 41.2 mmol) in THF (100 mL), 1,3-propanediol (22 g, 288-mmol), triethylorthoformate (18.3 g, 123.6 mmol) and Toluene-4-sulfonic acid (1 g, 0.2 mmol) were added at 25° C. The mixture was stirred at refluxed for 2 hour. The mixture was poured into aqueous NH$_4$Cl (400 mL), extracted with ethyl acetate (3×50 mL) and separated. The combined organic layers were washed with brine and dried over Na$_2$SO$_4$. The organic phase was concentrated in vacuo. The residue was purified by silica gel column chromatography (hexane:ether acetate=5:1) and the compound obtained (3.8 g) was dissolved in THF/H$_2$O (40 mL, 1:1). NaOH (2.52 g, 63 mmol) was added, the reaction mixture was stirred at room temperature for 1 hour and treated with ethyl acetate (20 mL). The combined inorganic layer was separated, pH=adjusted to 4 with 2N HCl, and extracted with CH$_2$Cl$_2$ (3×20 mL). The combined organic layer was washed with brine, dried over Na$_2$SO$_4$ and concentrated in vacuo resulting in compound PR-9 (5.9 g).

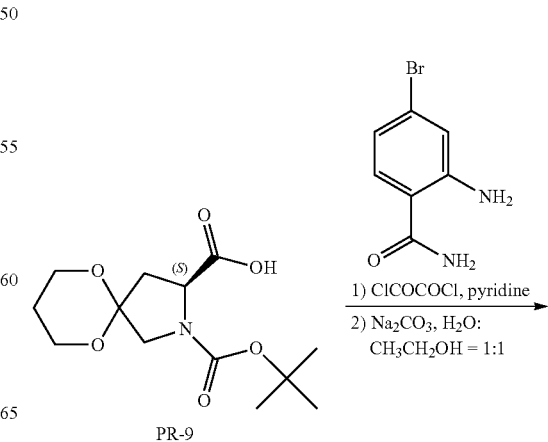

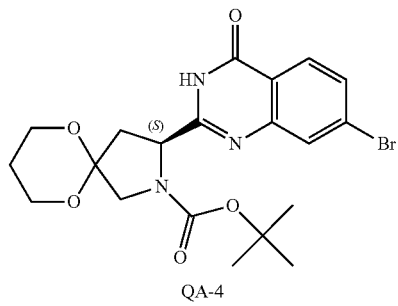

QA-4

Oxalyl dichloride (2.5 mL, 13.11 mmol) was added drop wise to a mixture of the compound PR-9 (2.5 g, 8.74 mmol), 2-amino-4-bromobenzamide (2.5 g, 10.49 mmol) in dichloromethane (20 mL) and pyridine (20 mL) at room temperature. The mixture was stirred for 1 hour at room temperature. The solvent was removed in vacuo. The residue was purified by column chromatography (petroleum ether:acetate ether=1:1). The obtained intermediate amide compound (0.98 g), Na$_2$CO$_3$ (1.08 g. 10.15 mmol), H$_2$O (5 mL) and CH$_3$CH$_2$OH (5 mL) were stirred for 2 hours under reflux. Most of CH$_3$CH$_2$OH was removed in vacuo and the obtained residue was extracted with ethyl acetate. The organic layer was dried over Na$_2$SO$_4$ and concentrated in vacuo. The residue was washed with t-butyl methyl ether resulting in compound QA-4 (0.89 g).

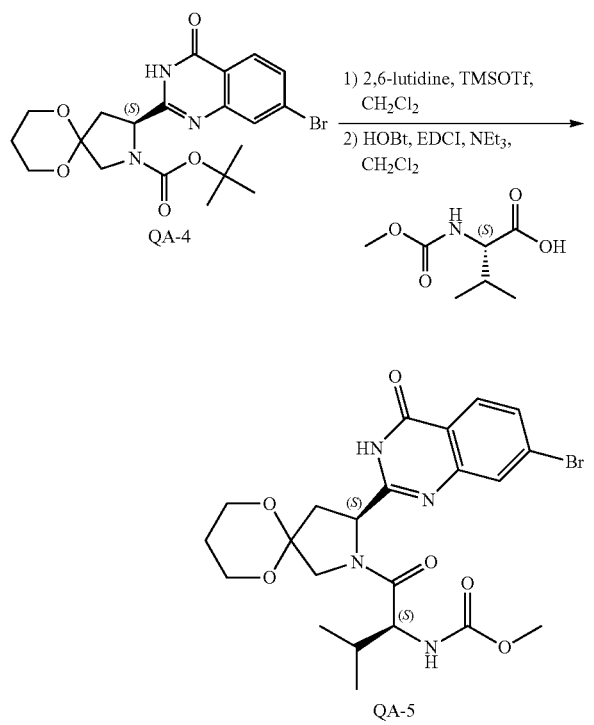

QA-5

To a stirred solution of compound QA-4 (0.89 g, 1.92 mmol) and lutidine (0.41 g, 3.84 mmol) in dry CH$_2$Cl$_2$ (10 mL) at 0° C. was added drop wise TMSOTf (1.7 g, 7.68 mmol). The reaction mixture was stirred at 0° C. for 30 minutes, quenched with saturated aqueous NH$_4$Cl, and extracted with ethyl acetate; the combined organic layers were washed with brine, dried over Na$_2$SO$_4$ and concentrated in vacuo. The obtained residue was used as such in the next reaction (0.3 g). Method A2; Rt: 0.68 min. m/z=:368.0 (M+H)$^+$ Exact mass: 367.0. NEt$_3$ (0.5 mL, 2.46 mmol) was added to the solution of the above obtained residue (0.3 g), (S)-2-(methoxycarbonylamino)-3-methylbutanoic acid (0.22 g, 1.23 mmol), HOBt (0.17 g, 1.23 mmol) and EDCI (0.24 g, 1.23 mmol) in dichloromethane (15 mL) in ice-water bath. The reaction mixture was stirred for 2 hours at room temperature. Then the mixture was diluted with dichloromethane (20 mL) and washed with Saturated NaHCO$_3$, brine and dried over Na$_2$SO$_4$. The solvent was removed in vacuo. The obtained residue was purified by column chromatography (hexane:ether acetate=1:1), resulting in compound QA-5 (0.2 g). Method A2; Rt: 1.14 min. m/z=:547.1 (M+Na)$^+$ Exact mass: 524.1

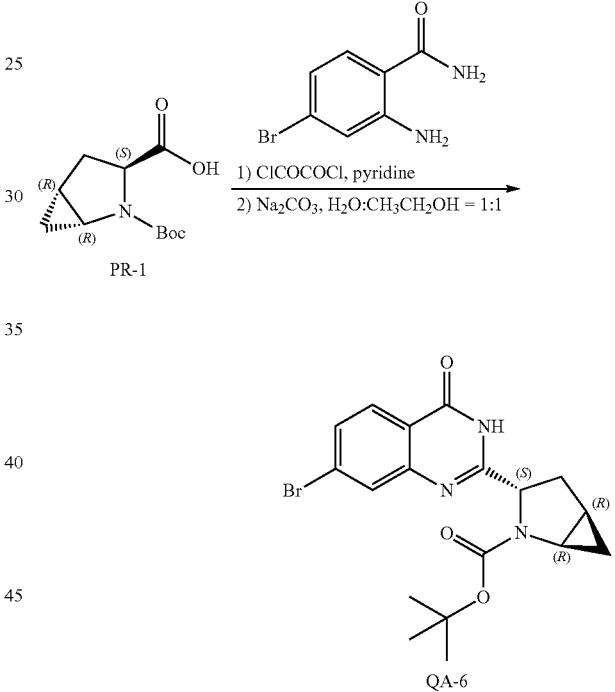

QA-6

Oxalyl chloride (2.9 mL, 33 mmol) was added drop wise to the mixture of compound PR-1 (5 g, 22 mmol), 2-amino-4-bromobenzamide (4.7 g, 22 mmol) and pyridine (50 mL). The mixture was stirred for 1 hour at room temperature. The solvent was removed in vacuo. The obtained residue was purified by chromatography (petroleum ether:acetate ether=5:1) resulting in an intermediate (3.6 g). Method A2; Rt: 1.15 min. m/z=:447.7 (M+Na)$^+$ Exact mass: 425.1 The above obtained intermediate (3.6 g), Na$_2$CO$_3$ (2.7 g. 25.4 mmol), H$_2$O (20 mL) and CH$_3$CH$_2$OH (20 mL) were stirred for 2 hours under reflux. Most of CH$_3$CH$_2$OH was removed in vacuo. The residue was extracted with ethyl acetate (3×20 mL). The organic layer was dried over Na$_2$SO$_4$ and concentrated in vacuo. The residue was washed with t-butyl methyl ether resulting in compound QA-6 (3.4 g)

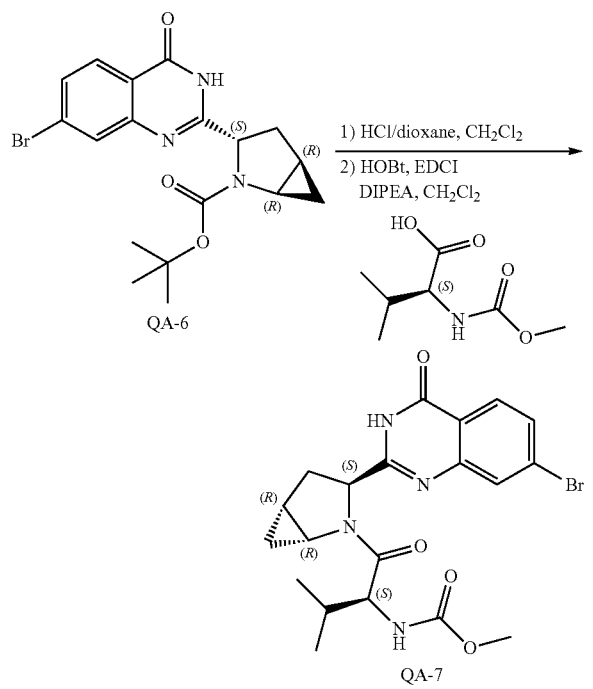

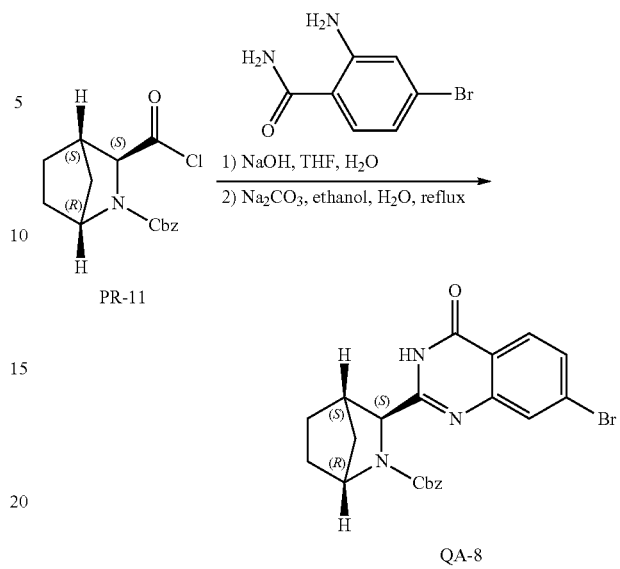

Compound QA-6 (3.4 g, 8.4 mmol) was dissolved in dichloromethane (30 mL) and HCl/dioxane (3 mL) was added drop wise to the mixture at 0° C. The reaction mixture was stirred for 5 hours at room temperature. The solvent was removed in vacuo. The residue was washed with t-butyl methyl ether and the obtained crude residue was used as such (2.7 g). To a solution of this crude (2.7 g), (S)-2-(methoxycarbonylamino)-3-methylbutanoic acid (2.75 g, 15.76 mmol), HOBt (2.42 g, 17.33 mmol) and EDCI (3.32 g, 17.33 mmol) in dichloromethane (20 mL) cooled in an ice-water bath, DIPEA (14 mL, 78.8 mmol) was added. The reaction mixture was stirred for 12 hours at room temperature. The mixture was diluted with dichloromethane (20 mL), washed with saturated NaHCO$_3$, brine and dried over Na$_2$SO$_4$. The solvent was removed in vacuo. The residue was purified by silica gel column chromatography (hexane:ether acetate=1:1), resulting in compound QA-7 (2.5 g). SFC: Column: AD-H 250 mm×4.6 mm; 5 um. Flow: 2.35 mL/min, Mobile phase: A: CO$_2$ B: EtOH (0.05% Diethylamine); 5 to 40% B in A,: Rt: 9.99 min

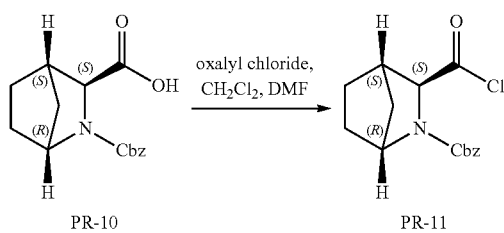

Compound PR-10 (2.0 g, 7.3 mmol) in CH$_2$Cl$_2$ (20 mL) was stirred at 0° C. Oxalyl dichloride (2.3 g, 18.2 mmol) and DMF (2 drops) were added dropwise and the mixture was stirred for 10 minutes at 0° C. The mixture was stirred for 1 hour at 20° C. The mixture was cooled and evaporated in vacuo. The residue was diluted twice with toluene (2×10 mL) and evaporated, resulting in a residue (PR-11, 2.5 g).

To the solution of compound PR-11 (2.5 g) in THF (30 mL) was added 2-amino-4-bromobenzamide e (1.57 g, 7.3 mmol) and 1N NaOH (14.6 mL, 14.6 mmol). The mixture was stirred for 1 hour at 25° C. The mixture was extracted with ethyl acetate (2×). The organic layers were combined, washed with 0.5 N NaOH, brine, dried and concentrated in vacuo, resulting in a residue (3.5 g) that was stirred with Na$_2$CO$_3$ (2.32 g, 21.9 mmol) in H$_2$O (50 mL) and THF (50 mL) and refluxed for 2 hours. The volatiles were removed in vacuo. The mixture was extracted with CH$_2$Cl$_2$ (2×), washed with brine, dried and the volatiles were removed in vacuo. The residue was dissolved in CH$_2$Cl$_2$ and washed with 1 N HCl (3×), brine, dried and the volatiles were removed in vacuo, resulting in compound QA-8 (1.5 g). Method A2; Rt: 1.15 min. m/z=:453.9 (M+H)$^+$ Exact mass: 453.1

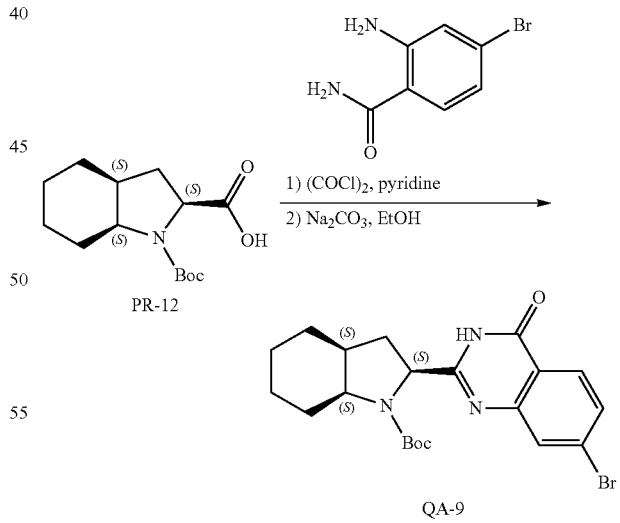

ClCOCOCl (44.4 mL, 510.2 mmol) was added dropwise to the mixture of PR-12 (100.6 g, 374 mmol), 2-amino-4-bromobenzamide (73.2 g, 340 mmol) and pyridine (760 mL) under nitrogen at 0° C. The mixture was stirred for 2 hour at room temperature. The solvent was removed in vacuo. To the residue was added saturated NaHCO$_3$ and the resulting mixture was extracted by ethyl acetate for three times. The combined organic layers were washed with saturated NaHCO$_3$, brine and dried over Na$_2$SO$_4$. The solvent was removed in vacuo. The obtained residue was purified by chromatography (CH$_2$Cl$_2$:MeOH=50:1) resulting in an intermediate amide compound (50.6 g). Method A2; Rt: 1.15 min. m/z=:490.1 (M+Na)$^+$ Exact mass: 467.1 A solution of the above obtained intermediate (50.61 g), Na$_2$CO$_3$ (34.51 g. 325.6 mmol), H$_2$O (300 mL) and CH$_3$CH$_2$OH (300 mL) was stirred for 3 hours at reflux. EtOH was removed in vacuo and the mixture was extracted with ethyl acetate (3×300 mL). The combined organic layers were dried over Na$_2$SO$_4$ and concentrated in vacuo. The obtained residue was washed with t-butyl methyl ether resulting in compound QA-9 (39.2 g).

Method A2; Rt: 1.37 min. m/z=:448.1 (M+H)$^+$ Exact mass: 447.1

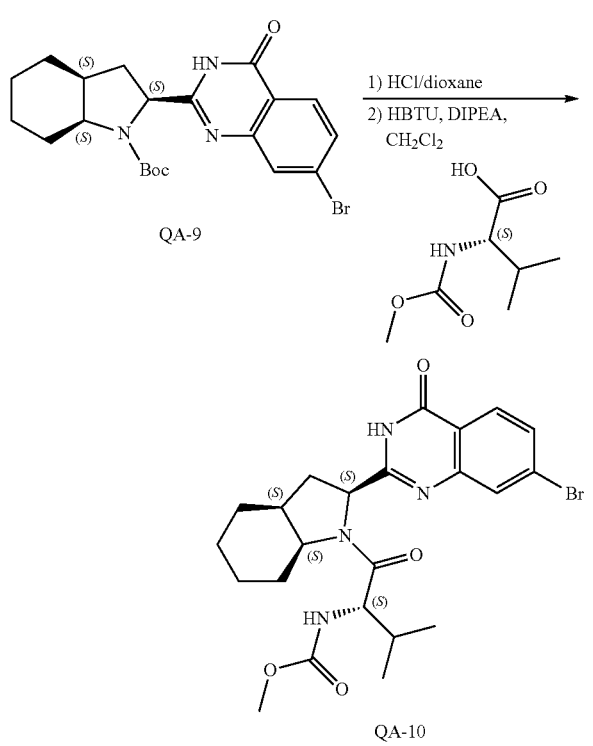

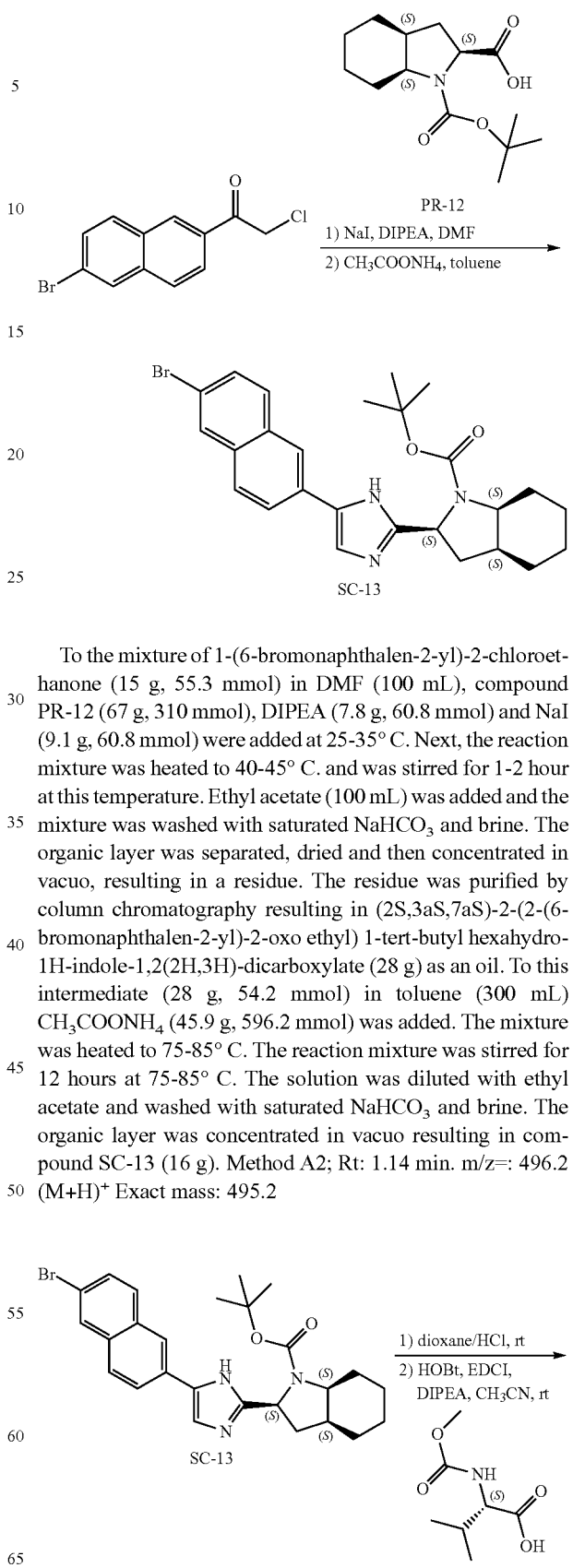

QA-9 (39.2 g, 87.5 mmol) was dissolved in dichloromethane (400 mL). HCl/dioxane (470 mL) was added dropwise to the mixture at 0° C. The reaction mixture was stirred for 3.5 hours at room temperature. The solvent was carefully removed in vacuo. The obtained residue was washed with t-butyl methyl ether, resulting in a residue (30.8 g) Method A2; Rt: 0.92 min. m/z=:348.1 (M+H)$^+$ Exact mass: 347.1

DIPEA (54.2 mL, 308 mmol) was added, at 0° C., to a solution of the above residue (30.84 g, 61.6 mmol), (S)-2-(methoxycarbonylamino)-3-methylbutanoic acid (11.9 g, 67.8 mmol) and HBTU (35.0 g, 92.4 mmol) in dichloromethane (265 mL) under nitrogen atmosphere. Next, the reaction mixture was stirred for 3 hours under nitrogen at room temperature. The reaction mixture was diluted with dichloromethane and washed with saturated. NaHCO$_3$, brine and dried over Na$_2$SO$_4$. The solvent was removed in vacuo. The residue was purified by column chromatography (petroleum ether:ethyl acetate=1:1), resulting in compound QA-10 (31.1 g). Method A2; Rt: 1.28 min. m/z=:507.2 (M+H)$^+$ Exact mass: 506.1

To the mixture of 1-(6-bromonaphthalen-2-yl)-2-chloroethanone (15 g, 55.3 mmol) in DMF (100 mL), compound PR-12 (67 g, 310 mmol), DIPEA (7.8 g, 60.8 mmol) and NaI (9.1 g, 60.8 mmol) were added at 25-35° C. Next, the reaction mixture was heated to 40-45° C. and was stirred for 1-2 hour at this temperature. Ethyl acetate (100 mL) was added and the mixture was washed with saturated NaHCO$_3$ and brine. The organic layer was separated, dried and then concentrated in vacuo, resulting in a residue. The residue was purified by column chromatography resulting in (2S,3aS,7aS)-2-(2-(6-bromonaphthalen-2-yl)-2-oxo ethyl) 1-tert-butyl hexahydro-1H-indole-1,2(2H,3H)-dicarboxylate (28 g) as an oil. To this intermediate (28 g, 54.2 mmol) in toluene (300 mL) CH$_3$COONH$_4$ (45.9 g, 596.2 mmol) was added. The mixture was heated to 75-85° C. The reaction mixture was stirred for 12 hours at 75-85° C. The solution was diluted with ethyl acetate and washed with saturated NaHCO$_3$ and brine. The organic layer was concentrated in vacuo resulting in compound SC-13 (16 g). Method A2; Rt: 1.14 min. m/z=: 496.2 (M+H)$^+$ Exact mass: 495.2

-continued

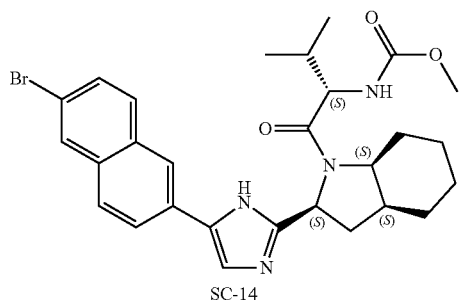

SC-14

To the solution of compound SC-13 (16 g, 32.3 mmol) was added dioxane/HCl at room temperature. The mixture was stirred for 1 hour at room temperature. The mixture was concentrated in vacuo. To the obtained residue CH$_2$Cl$_2$ (100 mL) was added, and the mixture was washed with saturated Na$_2$CO$_3$. The organic layer was separated and concentrated in vacuo, resulting in a deprotected intermediate (14 g).

To a solution of (S)-2-(methoxycarbonylamino)-3-methylbutanoic acid (7.9 g, 45.3 mmol) in CH$_3$CN (100 mL), HOBt (6.1 g, 45.3 mmol) and EDCI (8.6 g, 45.3 mmol) were added at room temperature. The mixture was stirred for 30 minutes at room temperature and then the above obtained deprotected intermediate (14 g) was added. Next, the solution was cooled to 0° C. and DIPEA (12.5 g, 97.2 mmol) was added. The mixture was stirred at room temperature overnight. The mixture was diluted with CH$_2$Cl$_2$ (200 mL) and washed with aqueous Na$_2$CO$_3$ (0.5 N, 100 mL) and brine. The organic layer was dried and concentrated, resulting in SC-14 (14 g)

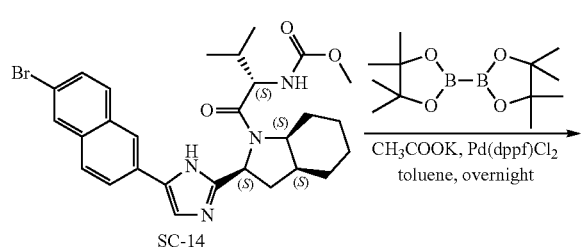

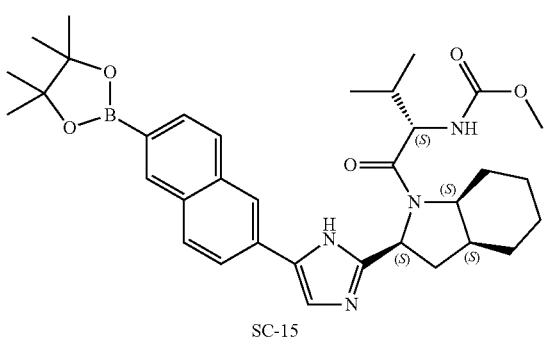

SC-15

The compound SC-14 (14 g, 25.3 mmol), 4,4,4',4',5,5,5', 5'-octamethyl-2,2'-bi(1,3,2-dioxaborolane) (12.9 g, 276 mmol) and CH$_3$COOK (4.96 g, 50.6 mmol) were stirred in toluene (100 mL). Pd (dppf) Cl$_2$ was added under N$_2$ atmosphere at room temperature. The reaction mixture was stirred at 80° C. overnight. After cooling, ethyl acetate (200 mL) was added and the mixture was washed with saturated NaHCO$_3$ (200 mL) and brine. The water layer was extracted with ethyl acetate. The combined organic layers were dried over Na$_2$SO$_4$ and concentrated in vacuo. The obtained residue was purified by column chromatography, resulting in compound SC-15 (15 g). Method A2; Rt: 1.17 min. m/z=: 601.4 (M+H)$^+$ Exact mass: 600.4

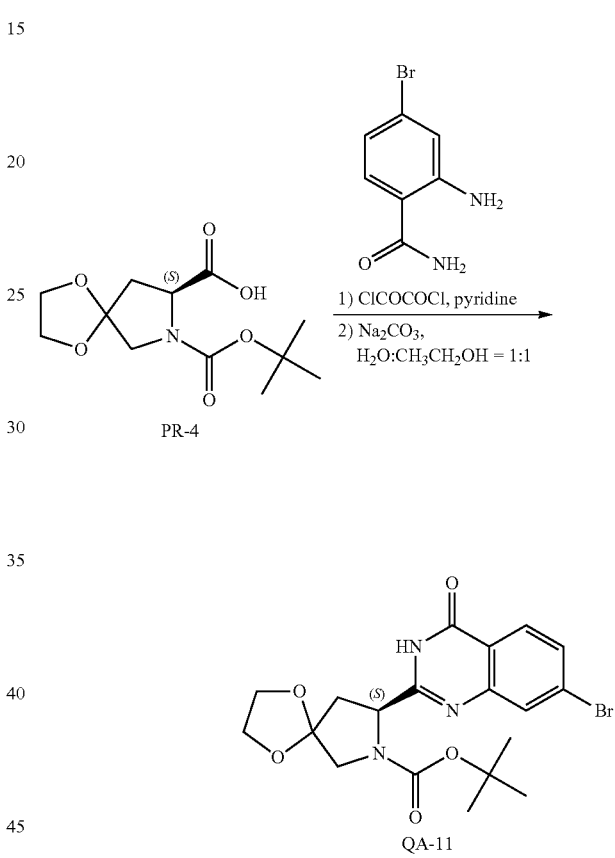

Oxalyl dichloride (2.5 mL, 13.11 mmol) was added drop wise to the mixture of compound PR-4 (3.3 g, 12 mmol), 2-amino-4-bromobenzamide (3.1 g, 14.5 mmol) in dichloromethane (30 mL) and pyridine (30 mL). The mixture was stirred for 1 hour at room temperature. The solvent was removed in vacuo and the obtained The residue was purified by chromatography (petroleum ether:acetate ether=1:1) resulting in an intermediate amide (0.7 g). This intermediate amide (0.7 g) Na$_2$CO$_3$ (0.82 g. 7.5 mmol), H$_2$O (10 mL) and CH$_3$CH$_2$OH (10 mL) was stirred for 2 hours at reflux. After cooling, most of CH$_3$CH$_2$OH was removed in vacuo. The residue was extracted with ethyl acetate. The organic layer was dried over Na$_2$SO$_4$ and concentrated in vacuo. The residue was washed with t-butyl methyl ether resulting in compound QA-11 (0.55 g). Method A2; Rt: 1.04 min. m/z=: 454.0 (M+H)$^+$ Exact mass: 453.1

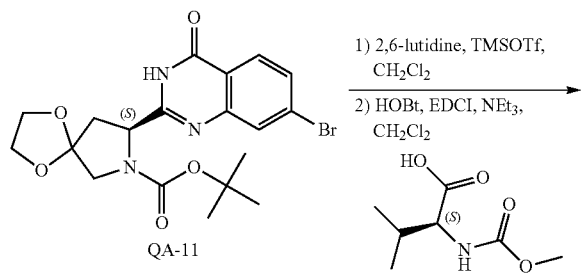
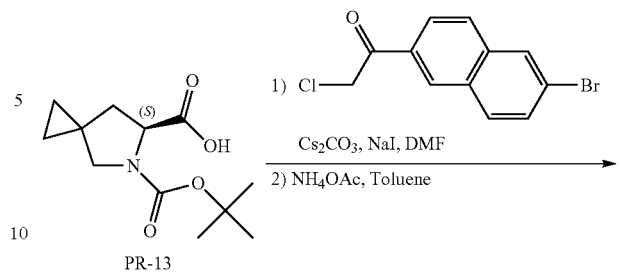

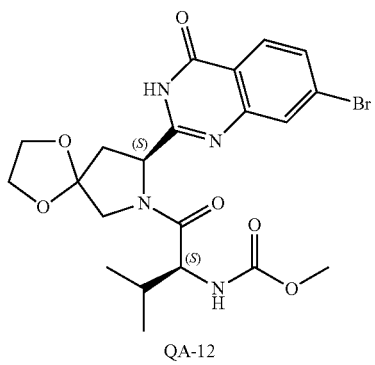
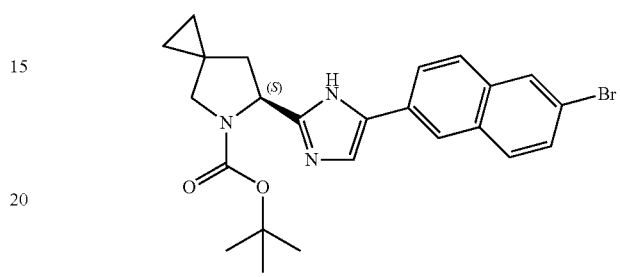

To a stirred solution of compound QA-11 (0.55 g, 1.2 mmol) and 2,6-lutidine (0.25 g, 2.4 mmol) in dry CH$_2$Cl$_2$ (5 mL) at 0° C., TMSOTf (1.1 g, 4.8 mmol) was added drop wise. The reaction mixture was stirred at 0° C. for 30 minutes, quenched with saturated aqueous NH$_4$Cl, and extracted with ethyl acetate. The combined organic layers were washed with brine, dried over Na$_2$SO$_4$ and concentrated in vacuo resulting in a residue (0.56 g). NEt$_3$ (0.24 g, 2.4 mmol) was added to the solution of the above obtained residue (0.56 g), (S)-2-(methoxycarbonylamino)-3-methylbutanoic acid (0.29 g, 1.4 mmol), HOBt (0.1 g) and EDCI (0.27 g, 1.4 mmol) in CH$_2$Cl$_2$ (10 mL) in ice-water bath. The reaction mixture was stirred for 2 hours at room temperature. Then, the mixture was diluted with dichloromethane (20 mL) and washed with Sat. NaHCO$_3$ and brine and finally dried over Na$_2$SO$_4$. The solvent was removed in vacuo. The residue was purified by silica gel column chromatography (hexane:ether acetate=1:1), resulting in compound QA-12 (0.3 g). Method A2; Rt: 1.11 min. m/z=: 511.1 (M+H)$^+$ Exact mass: 510.1

To a stirred solution of PR-13 (4.32 g, 17.9 mmol) in DMF (60 mL) was added Cs$_2$CO$_3$ (8.12 g, 26.9 mmol). The reaction mixture was stirred at 20° C. for 0.5 hours. Then, 1-(6-bromonaphthalen-2-yl)-2-chloroethanone (7.2 g, 26.85 mmol) and NaI (3.75 g, 26.85 mmol) were added and the mixture was further stirred at 20° C. for 2 hours. The mixture was washed with water (90 mL) and extracted with ethyl acetate (3×50 mL), the combined organic layers were washed with brine, dried over Na$_2$SO$_4$ and concentrated in vacuo. The residue was purified by column chromatography (hexane:ether acetate=5:1) to afford (S)-6-(2-(6-bromonaphthalen-2-yl)-2-oxoethyl) 5-tert-butyl 5-azaspiro[2.4]heptane-5,6-dicarboxylate (6.5 g). To a stirred solution of this compound (6.5 g) in toluene (60 mL) was added NH$_4$OAc (21.6 g, 267 mmol), and then the reaction mixture was stirred at 80° C. for 12 hours. The mixture was washed with water (50 mL) and extracted with ethyl acetate (3×30 mL); the combined organic layer was washed with brine, dried over Na$_2$SO$_4$ and concentrated in vacuo. The residue was purified by column chromatography (hexane:ethyl acetate=2:1) resulting in compound SC-16 (3.2 g). Method A2; Rt: 1.08 min. m/z=: 470.2 (M+H)$^+$ Exact mass: 469.1

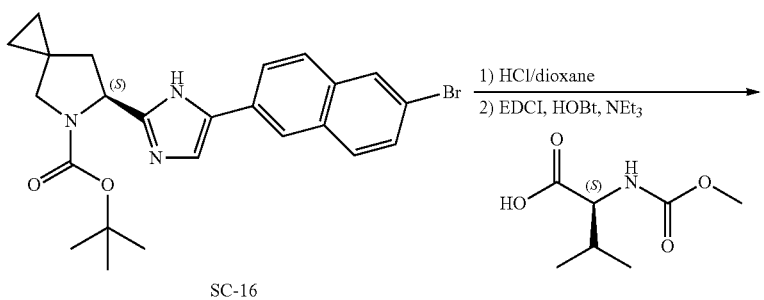

-continued

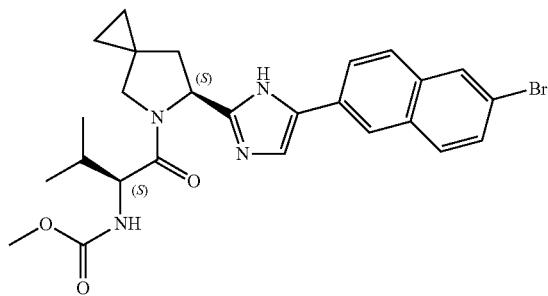

SC-17

Compound SC-16 (3.2 g, 6.85 mmol) in HCl/dioxane was stirred for 1 hour. The mixture was concentrated to dryness in vacuo and extracted with CH$_2$Cl$_2$. The combined organic layers were washed with brine, dried over Na$_2$SO$_4$ and concentrated in vacuo resulting in a residue (2.8 g). To this residue (2.8 g), (S)-2-(methoxycarbonylamino)-3-methylbutanoic acid (1.63 g, 9.16 mmol), EDCI (1.75 g, 9.16 mmol) and HOBt (1.24 g, 9.16 mmol) in dry CH$_2$Cl$_2$ (30 mL) was added NEt$_3$ (1.54 g, 15.26 mmol). The reaction mixture was stirred at 20° C. for 2 hours, quenched with saturated aqueous Na$_2$CO$_3$, and extracted with CH$_2$Cl$_2$ (3×20 mL). The combined organic layer was washed with brine, dried over Na$_2$SO$_4$ and concentrated in vacuo. The residue was purified by column chromatography (hexane:ether acetate=1:1) to afford compound SC-17 (3.2 g). Method A2; Rt: 1.03 min. m/z=: 527.2 (M+H)$^+$ Exact mass: 526.1

To a stirred solution of SC-17 (3.2 g, 6.1 mmol) and Pd (dppf) Cl$_2$ (0.4 g, 0.61 mmol) in dry dioxane (30 mL) was added 4,4,4',4',5,5,5',5'-octamethyl-2,2'-bi(1,3,2-dioxaborolane) (1.92 g, 7.32 mmol) and KOAc (1.2 g, 12.2 mmol). The reaction mixture was stirred at reflux for 20 minutes, quenched with water, and extracted with ethyl acetate (3×30 mL). The combined organic layer was washed with brine, dried over Na$_2$SO$_4$ and concentrated in vacuo. The residue was purified by column chromatography (hexane:ethyl acetate=1:1) resulting in compound SC-18 (2.7 g).

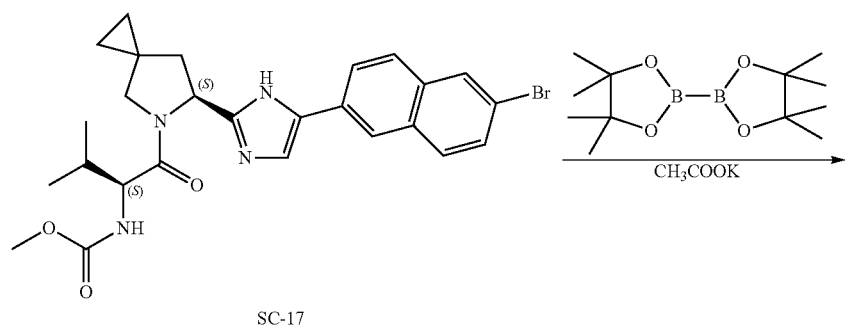

SC-17

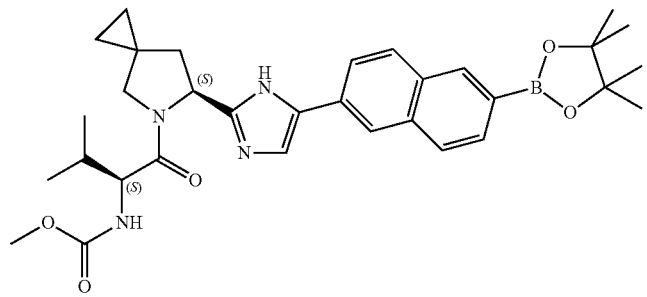

SC-18

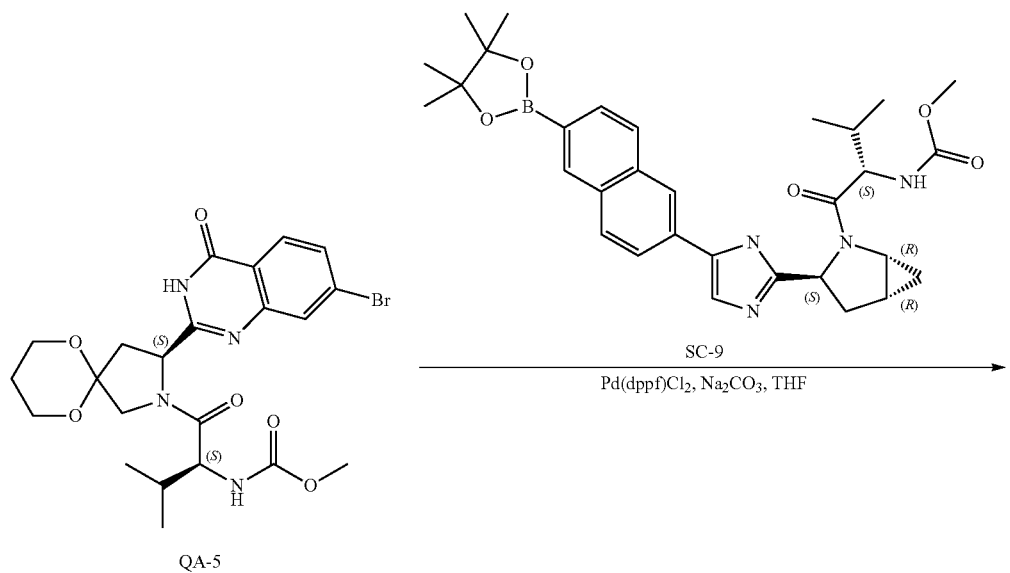

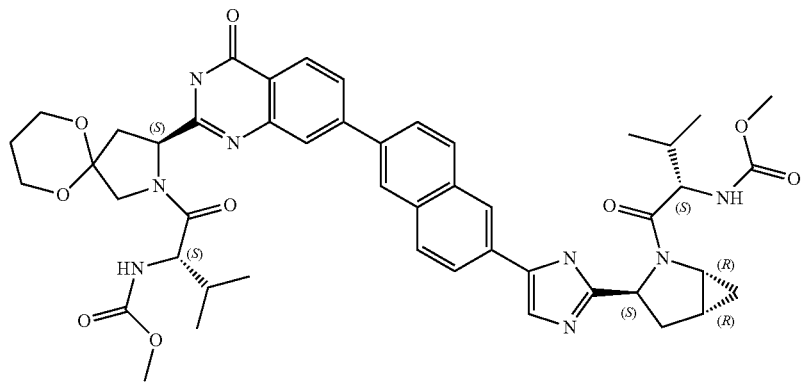

A mixture of compound QA-5 (0.2 g, 0.38 mmol), compound SC-9 (0.19 g, 0.32 mmol), Pd (dppf) Cl$_2$ (0.15 g, 0.032 mmol), Na$_2$CO$_3$ (5 mL, 2N) and THF (10 mL) were stirred for 0.5 hour at 80° C. under N$_2$. The volatiles were removed in vacuo. Dichloromethane (20 mL) and water (10 mL) were added. The organic layer was separated and dried over Na$_2$SO$_4$. The solvent was removed in vacuo, and the obtained crude was purified by high-performance liquid chromatography (Column: Diamonsil C18 150*20 mm*5 um. Method: From 20 to 40% B in A in 14 minutes. A: H$_2$O+0.1% TFA B: MeCN. FlowRate (mL/min):40). The pure fractions was collected and neutralized by saturated NaHCO$_3$. The organic solvent was removed in vacuo. The inorganic layer was extracted with ethyl acetate (3×10 mL). The combined organic layers were concentrated in vacuo resulting in compound 1 (60 mg) as an off-white powder. Method J; Rt: 4.66 min. m/z:875.5 (M+H)$^+$ Exact mass: 874.4; SFC: Column: AS-H 250 mm×4.6 mm; 5 um._Flow: 2.5 mL/min, Mobile phase: A: CO$_2$ B: MeOH (0.05% Diethylamine); 40% B in A,: Rt: 4.32 min

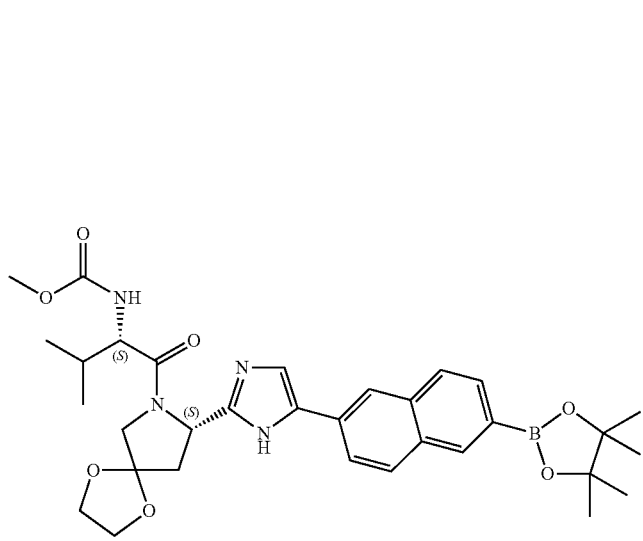

SC-12

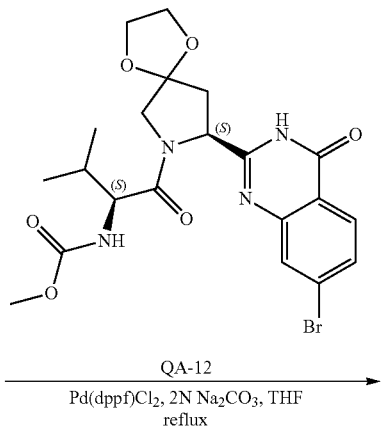

$\xrightarrow{\text{QA-12}}_{\text{Pd(dppf)Cl}_2,\text{ 2N Na}_2\text{CO}_3,\text{ THF reflux}}$

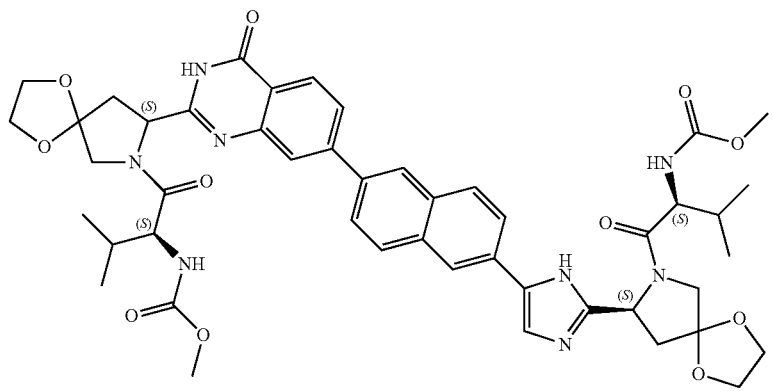

2

To a stirred solution of compound SC-12 (30 mg, 0.05 mmol), compound QA-12 (30 mg, 0.06 mmol) and Pd (dppf) Cl₂ (4 mg, 0.006 mmol) in dry THF (1 mL) was added Na₂CO₃ (0.5 mL, 2N). The reaction mixture was stirred at refluxed for 20 min, quenched with water (20 mL), and extracted with ethyl acetate (3×5 mL), the combined organic layer was washed with brine, dried over Na₂SO₄ and concentrated in vacuo. The residue was purified by high-performance liquid chromatography (Column: Phenomenex Synergi C18 150*30 mm*4 um. Method:From 30 to 50% B in A in 12 minutes. A: H₂O+0.1% TFA B: MeCN. Flow Rate (mL/min): 25). The pure fractions was collected and neutralized with saturated NaHCO₃. The organic solvent was concentrated in vacuo. The precipitate was filtered, washed with H₂O (10 mL) and dried under high vacuum, resulting in compound 2 (20 mg). Method J; Rt: 4.62 min. m/z:907.7 (M+H)⁺ Exact mass: 906.4; SFC: Column: OJ-H 250 mm×4.6 mm; 5 um. Flow: 2.35 mL/min, Mobile phase: A: CO₂ B: MeOH (0.05% Diethylamine); 5% to 40% B in A,: Rt: 9.88 min; SFC: Column: OD-H 150 mm×4.6 mm; 5 um._Flow: 2.35 mL/min, Mobile phase: A: CO₂ B: MeOH (0.05% Diethylamine); 40% B in A,: Rt: 8.34 min

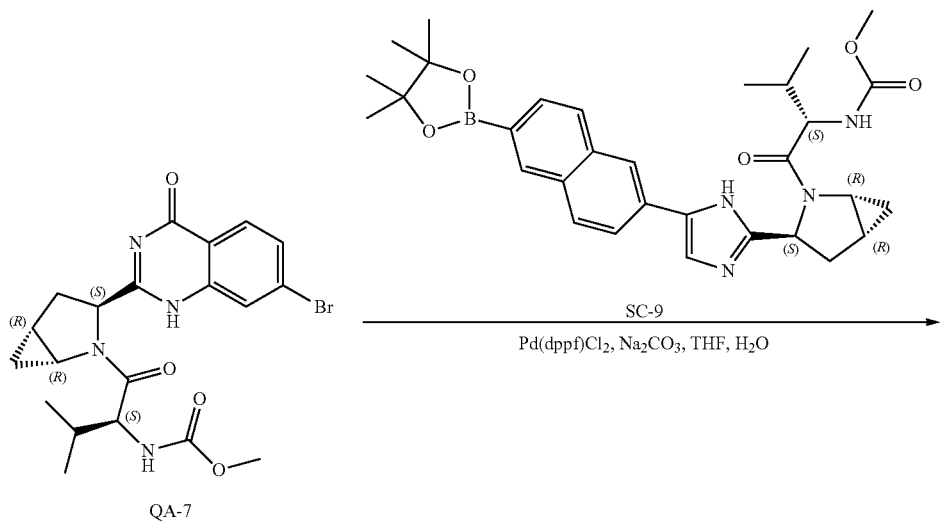

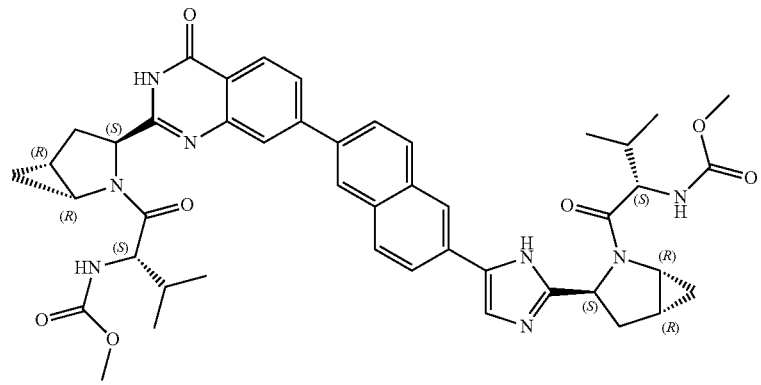

To a stirred solution of compound QA-7 (160 mg, 0.34 mmol), SC-9 (223 mg, 0.4 mmol) and Pd (dppf) Cl$_2$ (4 mg, 0.006 mmol) in dry THF (4 mL) was added Na$_2$CO$_3$ (2 mL, 2 N). The reaction mixture was stirred at refluxed for 20 minutes, quenched with water (20 mL), and extracted with ethyl acetate (3×5 mL), the combine organic layer was washed with brine, dried over Na$_2$SO$_4$ and concentrated in vacuo. The residue was purified by high-performance liquid chromatography (Column: Phenomenex Synergi C18 150*30 mm*4 um, Flow Rate (mL/min): 40 Mobile phase: A: H$_2$O+0.1% TFA B: MeCN, Gradient: 25-55%). The pure fractions was collected and neutralized by saturated NaHCO$_3$. The organic solvent was concentrated in vacuo. The precipitate was filtered, washed with H$_2$O (10 mL) and dried under high vacuum resulting in compound 3 (72 mg) product as yellow solid. Method H; Rt: 3.39 min. m/z:815.6 (M+H)$^+$ Exact mass: 814.4; SFC: Column: AS-H 250 mm×4.6 mm; 5 um. Flow: 2.35 mL/min, Mobile phase: A: CO$_2$ B: EtOH (0.05% Diethylamine); 40% B in A,: Rt: 3.40 min; SFC: Column: OD-H 250 mm×4.6 mm; 5 um._Flow: 2.35 mL/min, Mobile phase: A: CO$_2$ B: EtOH (0.05% Diethylamine); 40% B in A,: Rt: 8.16 min

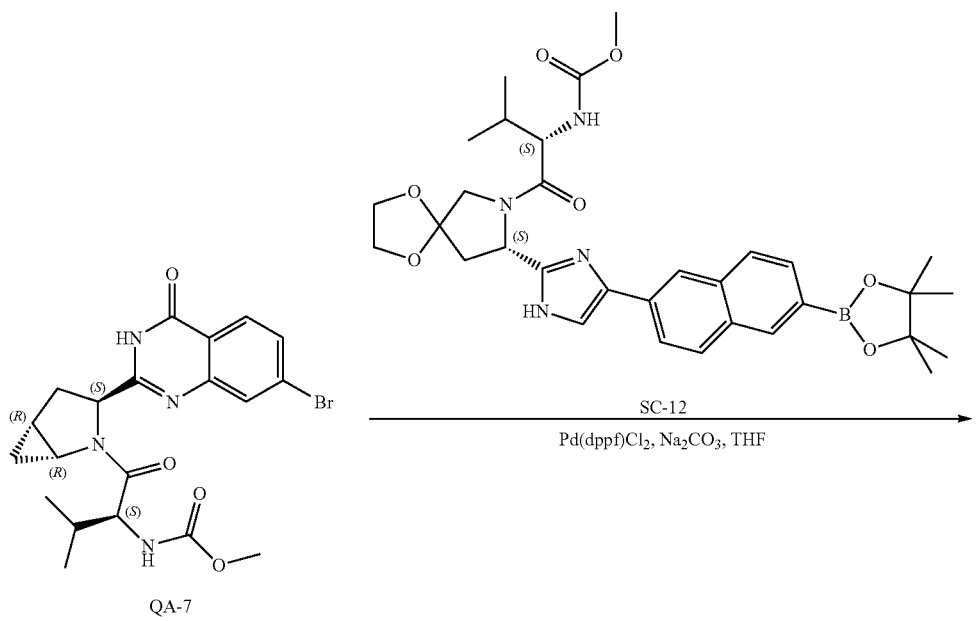

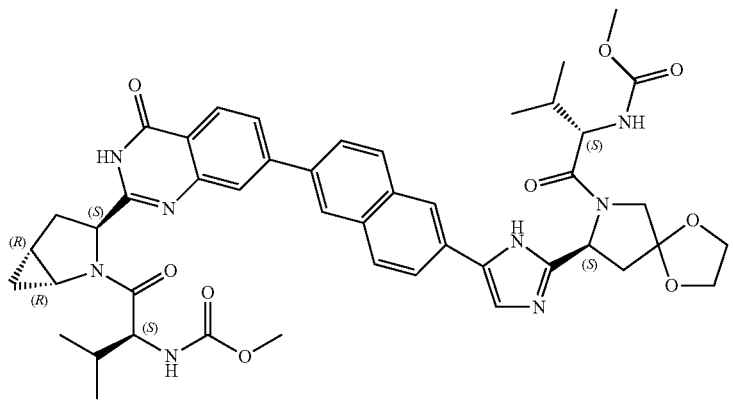

A mixture of compound QA-7 (0.184 g, 0.4 mmol), compound SC-12 (0.2 g, 0.33 mmol), Pd (dppf) Cl$_2$ (0.01 g, 0.014 mmol), Na$_2$CO$_3$ (5 mL 2N) and THF (10 mL) were stirred for 0.5 hour at 80° C. under N$_2$. The volatiles were removed in vacuo. Dichloromethane (20 mL) and water (10 mL) were added. The organic layer was separated and dried over Na$_2$SO$_4$. The solvent was removed in vacuo and the obtained residue was purified by high-performance liquid chromatography (Column: Diamonsil C18 150*20 mm*5 um. Method: From 20 to 40% B in A in 14 minutes. A: H$_2$O+0.1% TFA B: MeCN. FlowRate (mL/min): 40). The pure fractions were collected and neutralized by saturated NaHCO$_3$. The organic solvent was removed in vacuo. The inorganic layer was extracted with ether acetate (3×10 mL). The combined organic layers were concentrated in vacuo resulting in compound 4 (72 mg) as off-white powder. Method J; Rt: 4.66 min. m/z:861.7 (M+H)$^+$ Exact mass: 860.4; SFC: Column: OJ-H 250 mm×4.6 mm; 5 um._Flow: 2.35 mL/min, Mobile phase: A: CO$_2$ B: iPrOH (0.05% Diethylamine); 40% B in A,: Rt: 3.68 min

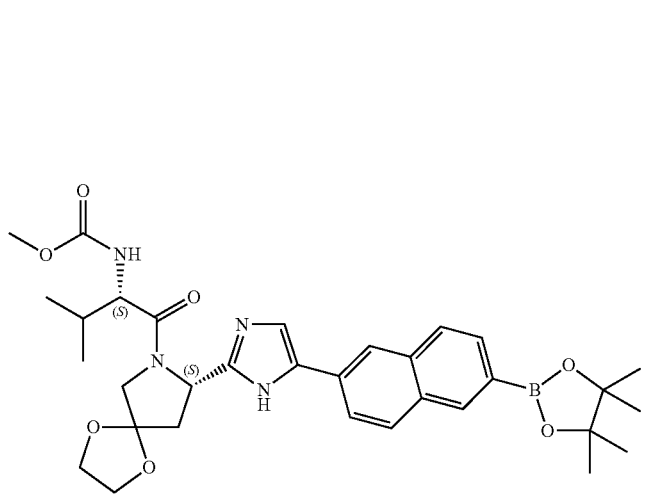

SC-12

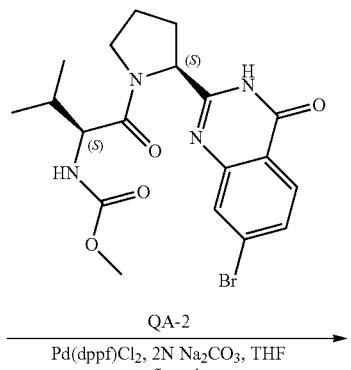

QA-2

$\xrightarrow{\text{Pd(dppf)Cl}_2,\ 2N\ \text{Na}_2\text{CO}_3,\ \text{THF}\ \text{refluxed}}$

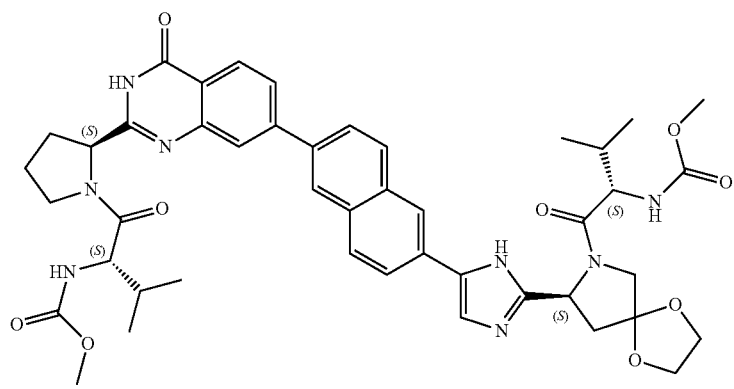

5

To a stirred solution of compound SC-12 (250 mg, 0.41 mmol), compound QA-2 (223 mg, 0.496 mmol) and Pd(dppf)Cl$_2$ (20 mg, 0.395 mmol) in dry THF (20 mL) Na$_2$CO$_3$ (10 mL, 2N) was added. The reaction mixture was stirred at reflux for 20 minutes, quenched with water (20 mL), and extracted with ethyl acetate (3×10 mL), the combined organic layer was washed with brine, dried on Na$_2$SO$_4$ and concentrated in vacuo. The residue was purified by high-performance liquid chromatography (Column: Phenomenex Synergi C18 200*30 mm*4 um. Method: From 31 to 51% B in A in 12 minutes. A: H$_2$O+0.1% TFA B: MeCN. FlowRate (mL/min): 40). The pure fractions was collected and neutralized with saturated NaHCO$_3$. The organic solvent was concentrated in vacuo. The precipitate was filtered, washed with H$_2$O (10 mL) and dried under high vacuum resulting in compound 5 (115 mg) as a solid. Method J; Rt: 4.65 min. m/z:849.5 (M+H)$^+$ Exact mass: 848.4; SFC: Column: OJ-H 250 mm×4.6 mm; 5 um._Flow: 2.5 mL/min, Mobile phase: A: CO$_2$ B: MeOH (0.05% Diethylamine); 40% B in A,: Rt: 10.1 min

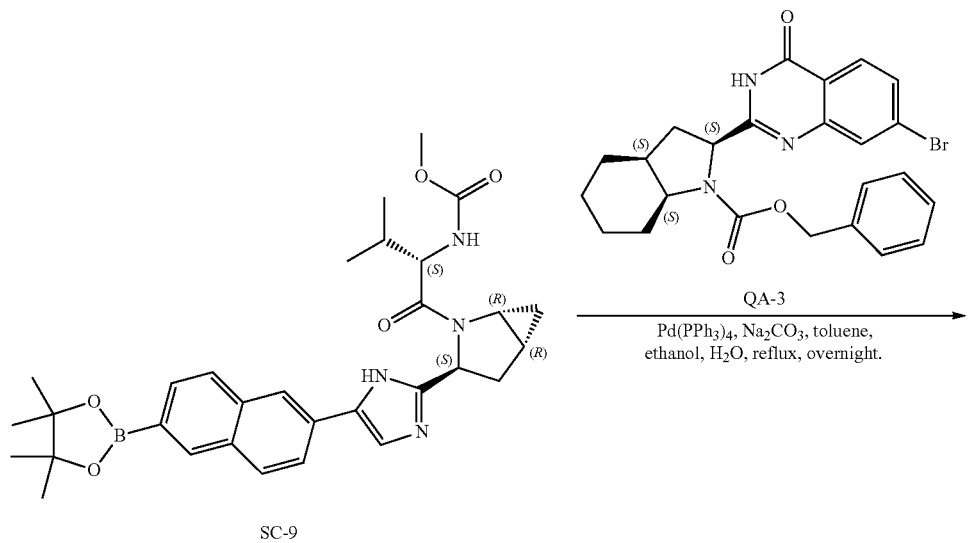

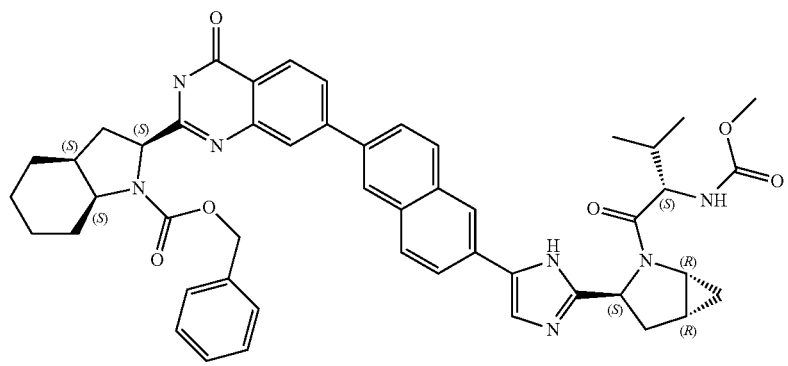

6

A mixture of compound SC-9 (1.0 g, 1.79 mmol), compound QA-3 (0.87 g, 1.79 mmol), Pd(PPh$_3$)$_4$ (0.21 g, 0.18 mmol) and Na$_2$CO$_3$ (1.52 g, 14.32 mmol) in toluene/ethanol/H$_2$O=1:1:1 (30 mL) was stirred for 2 hour at 100° C. under N$_2$. The volatiles were removed in vacuo. Dichloromethane (15 mL) and water (10 mL) were added. The organic layer was separated and dried over Na$_2$SO$_4$. The solvent was removed in vacuo. The obtained residue was purified by column chromatography on silica gel (Eluent: petroleum ether/ethyl acetate from 100/1 to 1/100). The pure fractions were collected and the solvent was concentrated in vacuo resulting in compound 6 (1.0 g). Method A; Rt: 1.02 min. m/z:834.5 (M+H)$^+$ Exact mass: 833.4;

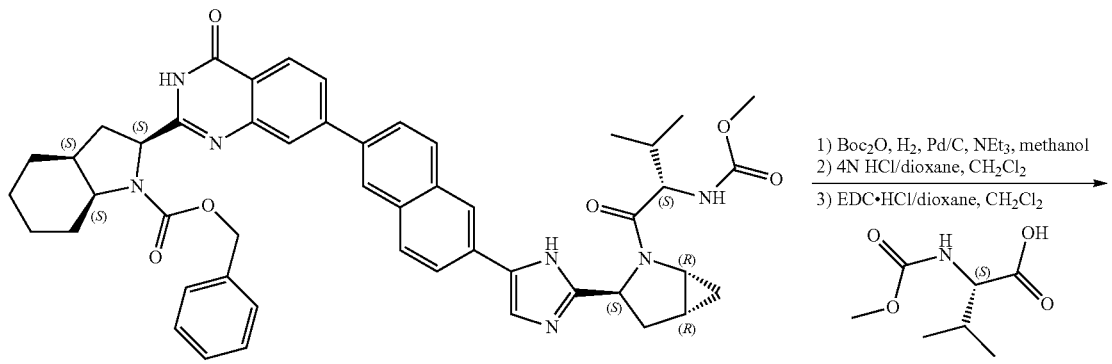

6

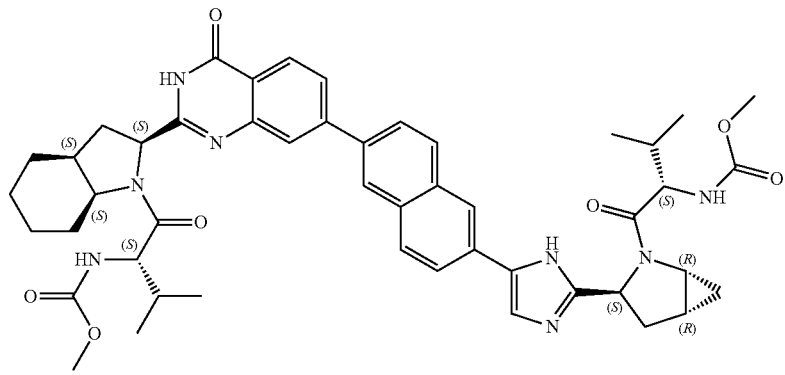

7

Compound 6 (1.0 g, 1.20 mmol), Boc₂O (0.52 g, 2.4 mmol), and NEt₃ (0.366 g, 3.60 mmol) in methanol (10 mL) were stirred with 10% Pd/C (wet) (0.1 g) 20° C.; under hydrogen atmosphere (30 Psi) for 24 hour. The catalyst was filtered off and the filtrate was concentrated in vacuo. The obtained residue (1.0 g) was dissolved in CH₂Cl₂ (10 mL) and stirred at 20° C. 4 N HCl/dioxane (10 mL) was added dropwise at 0° C. and the mixture was stirred at 25° C. for 1 hour. The solvent was removed in vacuo and the obtained residue, (S)-2-(methoxycarbonylamino)-3-methylbutanoic acid (0.46 g, 2.64 mmol), EDCI (0.51 g, 2.64 mmol) and HOBt (0.356 g, 2.64 mmol) in CH₂Cl₂ (10 mL) were stirred at 0° C. and DIPEA (1.55 g, 12 mmol) was added. The mixture was stirred at 20° C. for 12 hour. The mixture was diluted with CH₂Cl₂ (20 mL) and H₂O (50 mL). The organic layer was separated and washed with saturated aqueous NaHCO₃ (50 mL), brine and dried over Na₂SO₄. The solvent was removed in vacuo. The residue was purified by silica gel column chromatography (eluent: petroleum ether/ethyl acetate from 100/1 to 1/100). The pure fractions were collected and the solvent was concentrated in vacuo resulting in compound 7 (0.15 g). Method I; Rt: 3.83 min. m/z:857.6 (M+H)⁺ Exact mass: 856.4; SFC: Column: AS-H 250 mm×4.6 mm; 5 um. Flow: 2.5 mL/min, Mobile phase: A: CO₂ B: MeOH (0.05% Diethylamine); 40% B in A,: Rt: 4.1 min

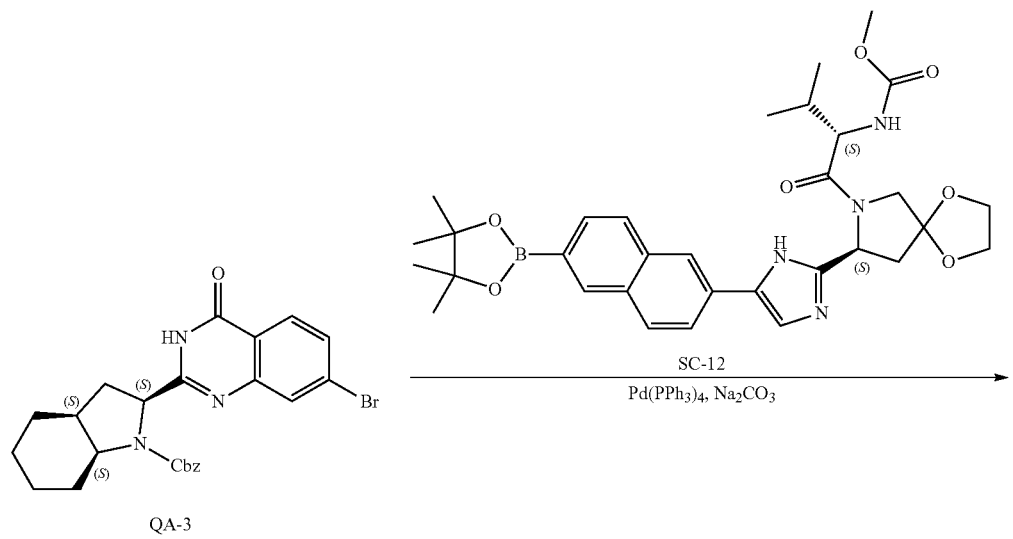

QA-3

-continued

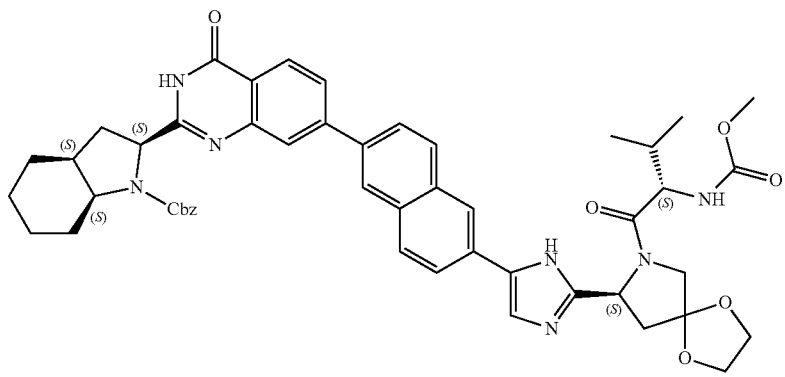

8

Compound QA-3 (0.5 g, 1 mmol), compound SC-12 (0.63 g, 1 mmol), Pd(PPh$_3$)$_4$ (0.35 g, 0.3 mmol) and Na$_2$CO$_3$ (0.42 g, 4 mmol) in toluene (5 mL), ethanol (5 mL) and H$_2$O (5 mL) were refluxed under N$_2$ for 12 hours. The solvent was removed in vacuo. The mixture was extracted with CH$_2$Cl$_2$ (2×) and the combined organic layers were washed with brine and dried on Na$_2$SO$_4$ After removal of the solvent in vacuo, the obtained residue was purified by silica gel column chromatography (eluent: petroleum ether/EtOAc=10/1 then 1/100 v/v). The pure fractions were collected and the solvent was concentrated in vacuo, resulting in compound 8 (0.55 g).

20

Compound 8 (0.55 g, 0.63 mmol), Boc$_2$O (0.27 g, 1.24 mmol) and triethylamine (0.19 g, 1.88 mmol) in CH$_3$OH (10 mL) were stirred with 10% Pd/C (0.15 g) as a catalyst at 20° C. under a hydrogen atmosphere (30 Psi) for 14 hours. The catalyst was filtered off and the filtrate was concentrated. The obtained crude product was dissolved in CH$_2$Cl$_2$ (5 mL). 4 N HCl/dioxane (5 mL) was added at 0° C. The mixture was stirred at 25° C. for 2 hours. The solvent was removed in vacuo. The residue was co-evaporated with toluene (2×5 mL) resulting in 0.5 g deprotected intermediate. This product (0.5 g), (S)-2-(methoxycarbonylamino)-3-methylbutanoic acid

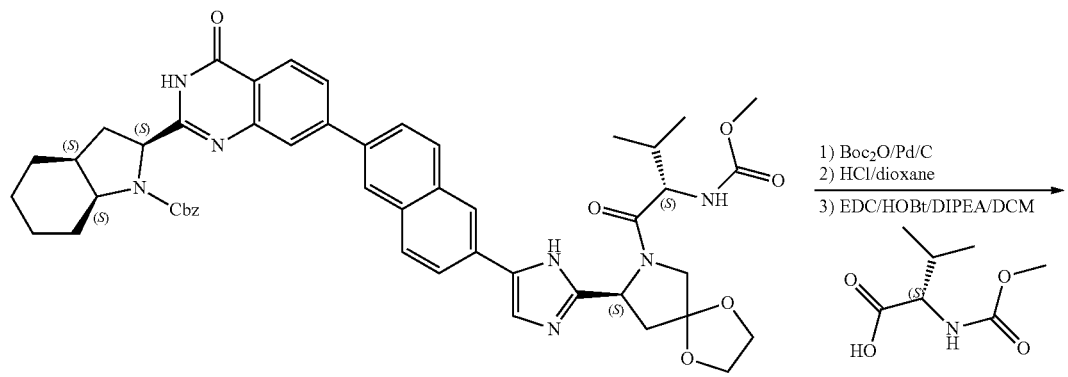

8

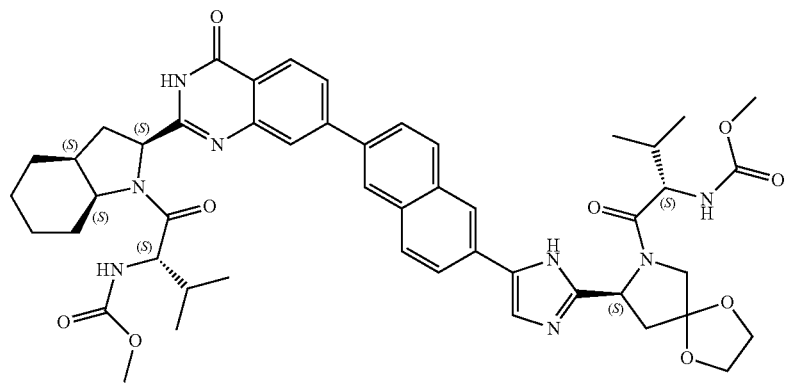

9

(0.13 g, 0.74 mmol), EDCI (0.18 g, 0.94 mmol) and HOBt (0.042 g, 0.31 mmol) in CH₂Cl₂ (5 mL) were stirred at 0° C. DIPEA (0.4 g, 3.1 mmol) was added. The mixture was stirred for 2 hour at 20° C. The mixture was washed with H₂O (2×5 mL) and brine (5 mL), dried on Na₂SO₄ and the obtained solution was concentrated to dryness in vacuo. The residue was purified by high-performance liquid chromatography (C18, eluent: CH₃CN/H₂O from 15/85 to 35/65 with 0.1% CF₃COOH as buffer). The pure fractions were collected and the mixture was basified with NaHCO₃ to pH=9. The organic solvent was evaporated, the precipitate was filtered off and dried in vacuo, resulting in compound 9 as a solid (0.12 g). Method H; Rt: 3.80 min. m/z: 903.6 (M+H)⁺ Exact mass: 902.4 SFC: Column: AS-H 250 mm×4.6 mm; 5 um._Flow: 2.35 mL/min, Mobile phase: A: CO₂ B: MeOH (0.05% Diethylamine); 40% B in A,: Rt: 3.68 min; ¹H NMR (600 MHz, DMSO-d₆) δ ppm 0.81 (d, J=6.6 Hz, 3H), 0.86 (d, J=6.7 Hz, 3H), 0.88 (d, J=6.5 Hz, 3H), 0.94 (d, J=6.7 Hz, 3H), 1.18-1.36 (m, 2H), 1.46 (d, J=10.3 Hz, 1H), 1.60-1.71 (m, 1H), 1.72-1.80 (m, 2H), 1.82-1.90 (m, 1H), 1.92-1.98 (m, 1H), 1.98-2.06 (m, 2H), 2.06-2.16 (m, 1H), 2.19-2.28 (m, 1H), 2.34-2.42 (m, 1H), 2.46 (d, J=8.2 Hz, 2H), 3.54 (s, 3H), 3.55 (s, 3H), 3.80 (d, J=11.2 Hz, 1H), 3.88 (dd, J=9.4, 8.8 Hz, 1H), 3.90-4.05 (m, 5H), 4.07 (d, J=10.9 Hz, 1H), 4.37-4.55 (m, 1H), 4.75 (t, J=8.9 Hz, 1H), 5.11 (t, J=8.4 Hz, 1H), 7.35 (d, J=8.7 Hz, 1H), 7.55 (d, J=8.2 Hz, 1H), 7.71 (br. s., 1H), 7.75 (s, 1H), 7.87 (br. s., 1H), 7.92 (dd, J=8.3, 1.5 Hz, 1H), 7.95 (d, J=8.4 Hz, 1H), 8.03 (d, J=8.5 Hz, 1H), 8.04-8.10 (m, 1H), 8.20 (d, J=8.2 Hz, 1H), 8.24-8.34 (m, 2H), 11.99 (br. s., 1H), 12.40 (s, 1H)

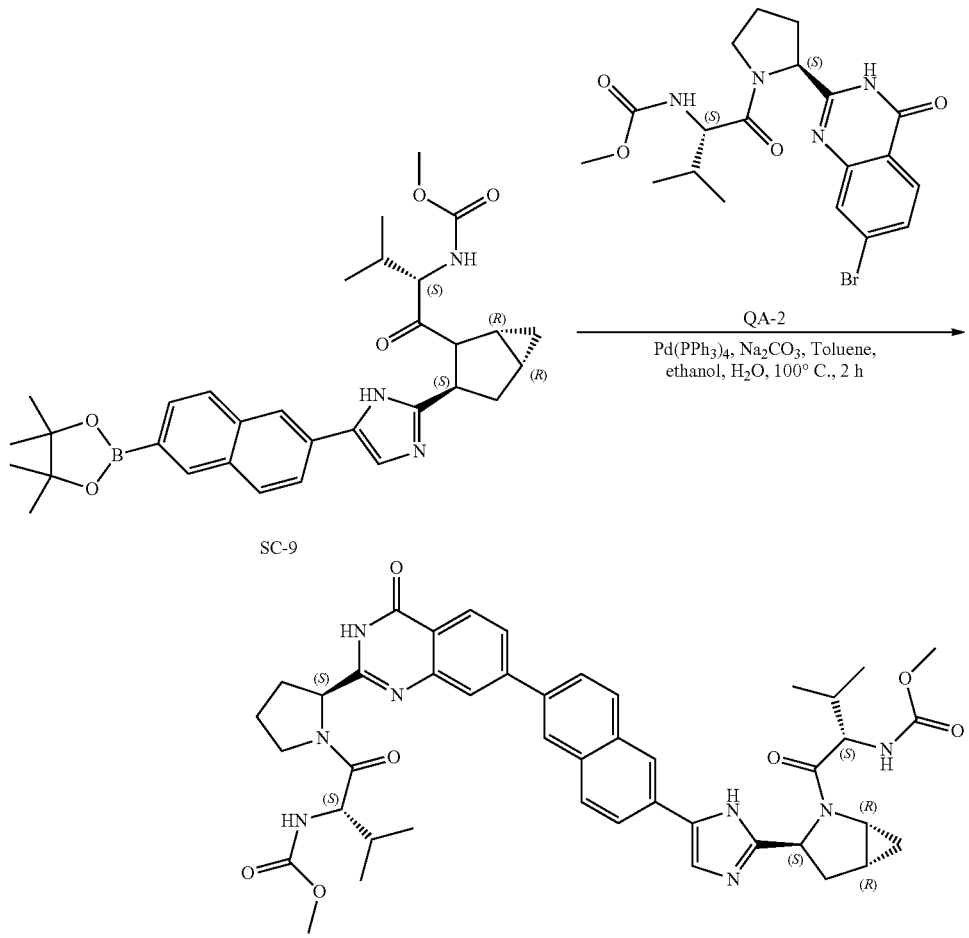

A mixture of compound SC-9 (1.0 g, 1.79 mmol), compound QA-2 (0.8 g, 1.79 mmol), Pd(PPh₃)₄ (0.21 g, 0.18 mmol) and Na₂CO₃ (1.52 g, 14.32 mmol) in toluene/ethanol/H₂O=1:1:1 (30 mL) were stirred for 2 hour at 100° C. under N₂. The volatiles were removed in vacuo. Dichloromethane (100 mL) and water (40 mL) were added. The organic layer was separated and dried on Na₂SO₄. The solvent was removed in vacuo. From the obtained yellow powder (1.0 g), part (600 mg) was purified by high-performance liquid chromatography (Column: Phenomenex Synergi C18 150*30 mm*4 um. Method: From 20 to 50% B in A in 11 minutes. A: H₂O+0.1% TFA B: MeCN. FlowRate (mL/min):40). The pure fractions were collected and neutralized by saturated NaHCO₃. The organic solvent was removed in vacuo. The precipitate was filtered, washed with H₂O (10 mL) and dried under high vacuum, resulting in compound 10 as an off-white powder (360 mg). Method H; Rt: 3.39 min. m/z: 803.4 (M+H)⁺ Exact mass: 802.4; SFC: Column: AS-H 250 mm×4.6 mm; 5 um._Flow: 2.35 mL/min, Mobile phase: A: CO₂ B: MeOH (0.05% Diethylamine); 5 to 40% B in A,: Rt: 9.48 min

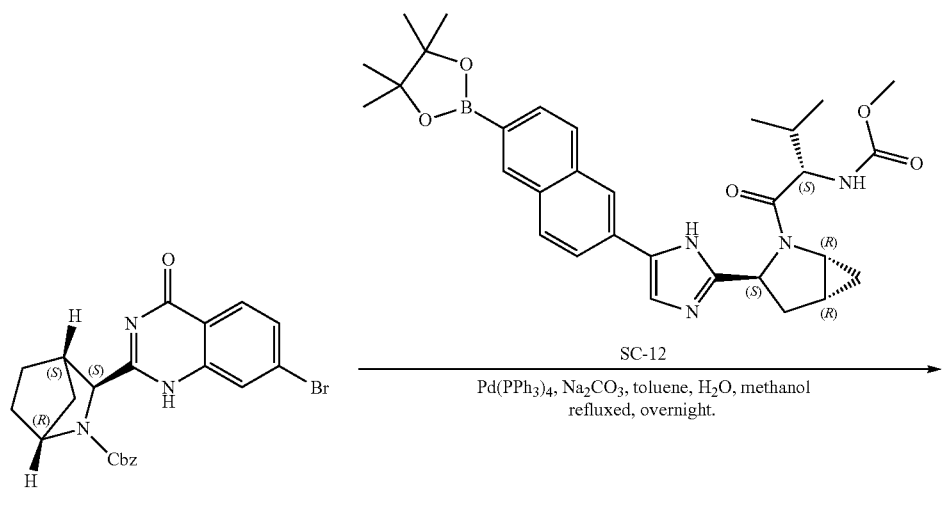

Compound QA-8 (0.5 g, 1.1 mmol), compound SC-12 (0.62 g, 1.1 mmol), Pd(PPh$_3$)$_4$ (0.38 g, 0.33 mmol) and Na$_2$CO$_3$ (0.47 g, 4.4 mmol) in toluene (5 mL), CH$_3$CH$_2$OH (5 mL) and H$_2$O (5 mL) were refluxed under N$_2$ for 12 hours. The solvent was removed in vacuo. The mixture was extracted with CH$_2$Cl$_2$ (2×20 mL) and the organic layers were washed with brine and dried. The residue was purified by silica gel column chromatography (eluent: petroleum ether/ethyl acetate=10/1 then 1/100 v/v). The pure fractions were collected and the solvent was removed in vacuo, resulting in compound 11 (0.35 g).

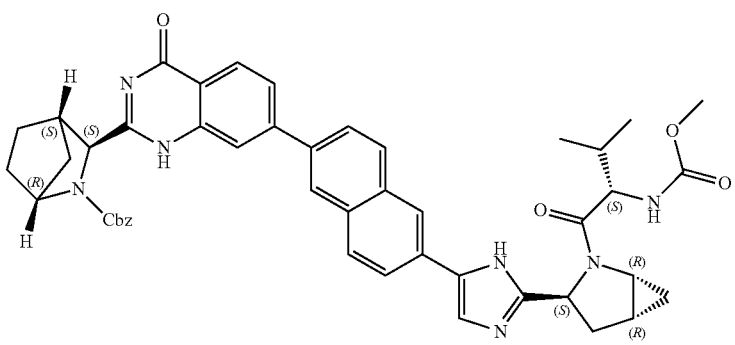

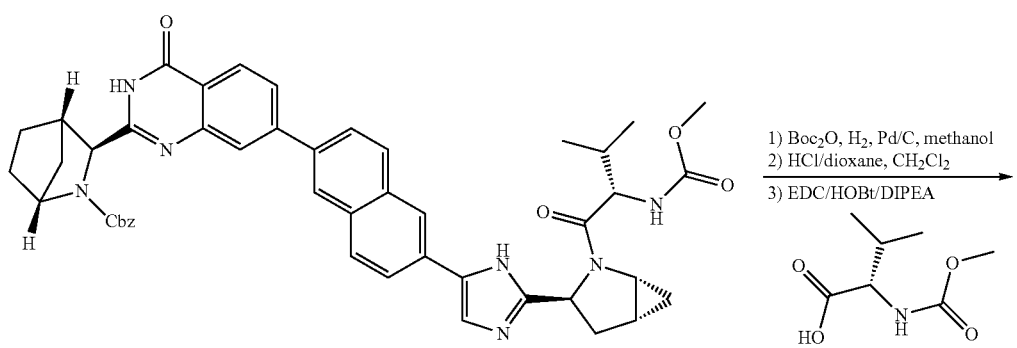

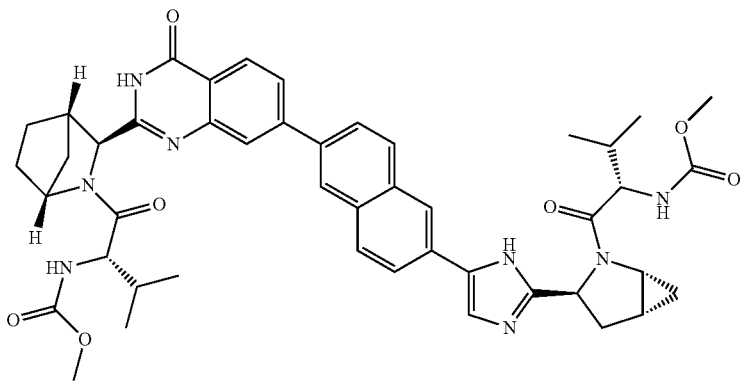

12

Compound 11 (0.35 g, 0.44 mmol), Boc$_2$O (0.19 g, 0.88 mmol) and NEt$_3$ (0.13 g, 1.32 mmol) in CH$_3$OH (10 mL) were hydrogenated with 10% Pd/C (0.1 g) as a catalyst at 20° C. (30 Psi) for 14 hours. After completion, the catalyst was filtered off and the volatiles were removed in vacuo, resulting in a residue (0.3 g). This residue (0.3 g) was dissolved in CH$_2$Cl$_2$ (5 mL) and 4M HCl/dioxane (3 mL) was added at 0° C. The mixture was stirred at 25° C. for 2 hours. The solvent was removed in vacuo and the obtained residue was twice diluted with toluene (2×5 mL) followed by removal of toluene, resulting in a residue (0.3 g). This residue (0.3 g), (S)-2-(methoxycarbonylamino)-3-methylbutanoic acid (0.093 g, 0.53 mmol), EDCI (0.13 g, 0.66 mmol) and HOBt (0.030 g, 022 mmol) in CH$_2$Cl$_2$ (5 mL) were stirred at 0° C. DIPEA (0.28 g, 2.2 mmol) was added and the mixture was stirred for 2 hours at 20° C. The mixture was washed with H$_2$O (2×5 mL) and brine, dried on Na$_2$SO$_4$ and the volatiles were removed in vacuo. The residue was purified by high-performance liquid chromatography (C18, eluent: CH$_3$CN/H$_2$O from 15/85 to 35/65 with 0.1% CF$_3$COOH as buffer). The pure fractions were collected and the mixture was basified with NaHCO$_3$ to pH=9. The organic solvent was evaporated and the precipitate was filtered. The solid was dried in vacuo and then purified by SFC chromatography (Chiralcel AD-H, 20 μm; Supercritical CO$_2$: MeOH, v/v, 200 mL/min). The pure fractions were collected and the solvent was removed in vacuo, resulting in compound 12 (0.06 g). Method H; Rt: 3.5 min. m/z:829.5 (M+H)$^+$ Exact mass: 828.4;

SFC: Column: AS-H 250 mm×4.6 mm; 5 um._Flow: 2.5 mL/min, Mobile phase: A: CO$_2$ B: EtOH (0.05% Diethylamine); 40% B in A,: Rt: 3.67 min

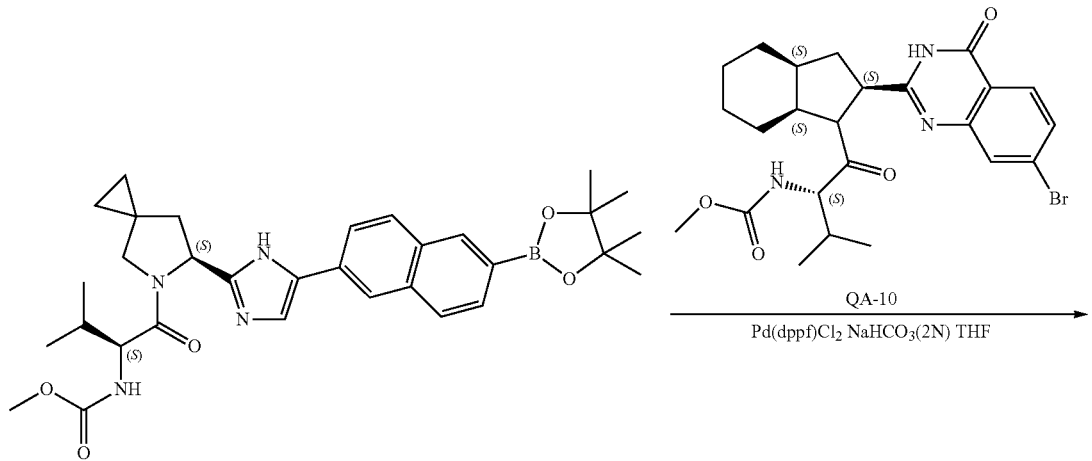

SC-18

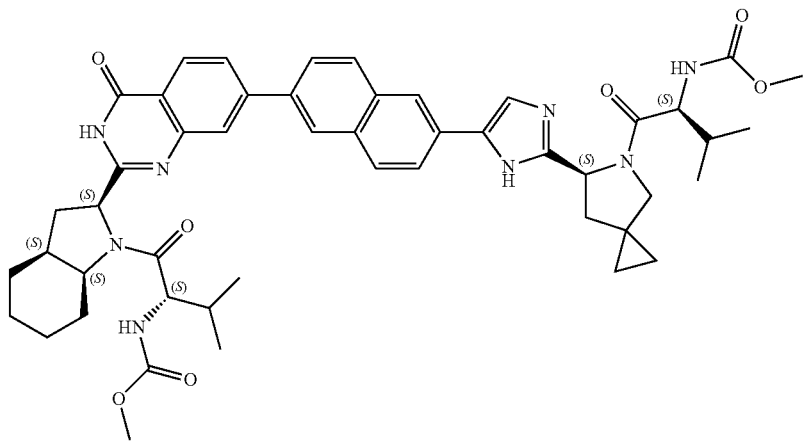

13

To a stirred solution of SC-18 (1.4 g, 2.45 mmol), QA-10 (1.49 g, 2.94 mmol) and Pd (dppf)Cl$_2$ (0.2 g, 0.245 mmol) in dry THF (30 mL) was added NaHCO$_3$ (15 mL, 2N). The reaction mixture was stirred at reflux for 20 minutes, quenched with water (20 mL), and extracted with ethyl acetate (3×20 mL). The combined organic layer was washed with brine, dried over Na$_2$SO$_4$ and concentrated in vacuo. The residue was purified by high-performance Liquid chromatography. (Column: Diamonsil C18 250*50 mm*10 um. Method: A: H$_2$O+0.1% TFA B: CH$_3$CN, From 25 to 40% B in A in 17 minutes. FlowRate (mL/min):90). The pure fraction was collected and neutralized by saturated NaHCO$_3$. The mixture was extracted with CH$_2$Cl$_2$ (3×20 mL). The combined organic layers were concentrated in vacuo resulting in compound 13 (600 mg). Method H; Rt: 3.92 min. m/z:871.6 (M+H)$^+$ Exact mass: 870.4;

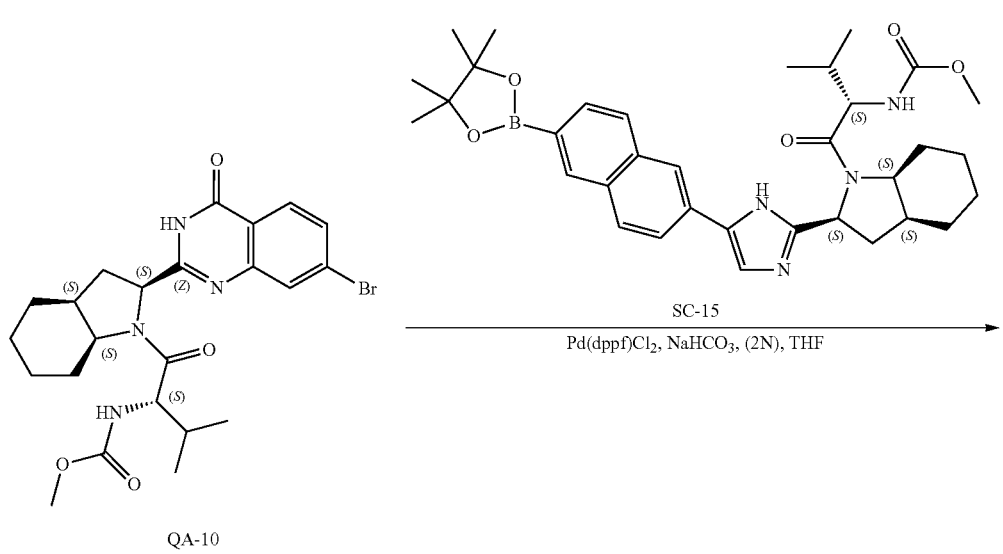

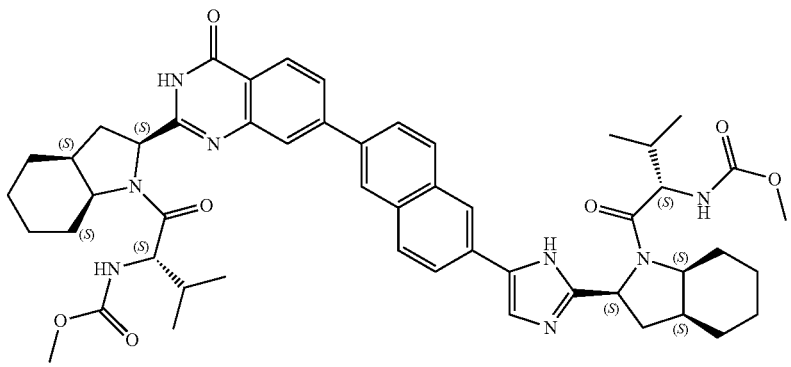

14

To a stirred solution of compound QA-10 (2.5 g, 4.96 mmol), compound SC-15 (2.5 g, 4.13 mmol) and Pd (dppf) Cl₂ (0.2 g, 0.496 mmol) in dry THF (30 mL) was added NaHCO₃ (15 mL, 2 N). The reaction mixture was stirred at reflux for 20 minutes, quenched with water (20 mL), and extracted with ethyl acetate (3×20 mL). The combined organic layer were washed with brine, dried over Na₂SO₄ and concentrated in vacuo. The residue was purified by high-performance Liquid chromatography. (Column: Diamonsil C18 250*50 mm*10 um. Method: A: H₂O+0.1% TFA B: CH₃CN. From 25 to 40% B in A in 17 minutes. FlowRate (mL/min):90). The pure fraction was collected and neutralized by saturated NaHCO₃. The organic solvent was concentrated in vacuo. The precipitate was filtered, washed with H₂O (10 mL) and dried under high vacuum to afford compound 14 (1000 mg). Method H; Rt: 4.11 min. m/z:899.5 (M+H)⁺ Exact mass: 898.5; SFC: Column: AS-H 250 mm×4.6 mm; 5 um._Flow: 2.5 mL/min, Mobile phase: A: CO₂ B: MeOH (0.05% Diethylamine); 40% B in A,: Rt: 5.1 min; SFC: Column: OJ-H 250 mm×4.6 mm; 5 um._Flow: 2.5 mL/min, Mobile phase: A: CO₂ B: MeOH (0.05% Diethylamine); 40% B in A,: Rt: 3.14 min

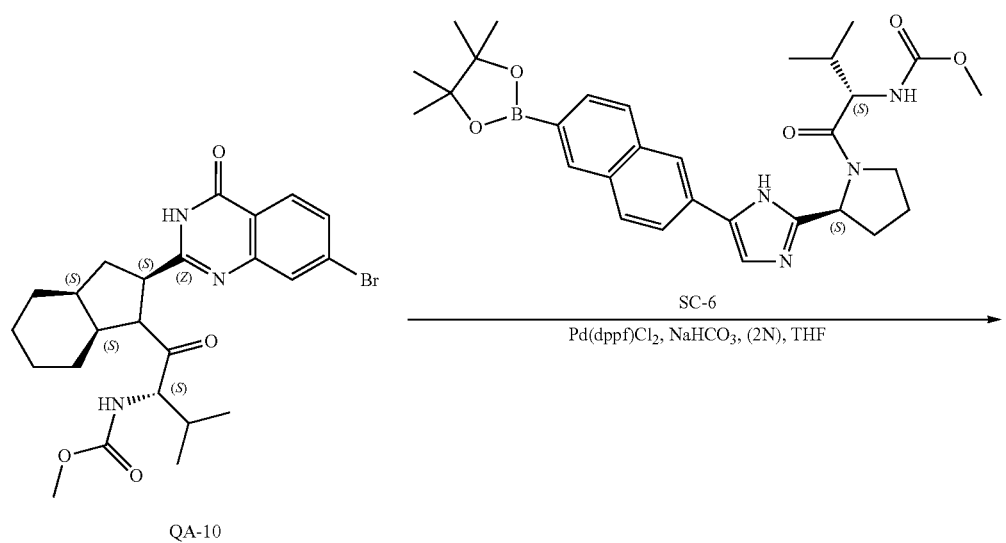

-continued

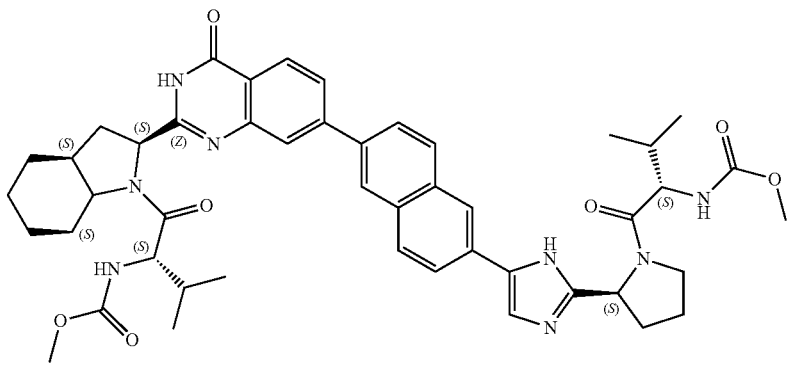

15

To a stirred solution of QA-10 (2.0 g, 3.97 mmol), compound SC-6 (1.8 g, 3.31 mmol) and Pd (dppf)Cl$_2$ (0.2 g, 0.397 mmol) in dry THF (20 mL) was added NaHCO$_3$ (10 mL, 2 N). The reaction mixture was stirred at reflux for 20 minutes, quenched with water (20 mL), and extracted with ethyl acetate (3×20 mL). The combined organic layer was washed with brine, dried over Na$_2$SO$_4$ and concentrated in vacuo. The resulting residue was purified by high-performance Liquid chromatography. (Column: Diamonsil C18 250*50 mm*10 um. Method: A: H$_2$O+0.1% TFA B: CH$_3$CN. 25 to 40% B in A in 17 minutes. FlowRate (mL/min):90). The pure fraction was collected and neutralized by saturated NaHCO$_3$. The organic solvent was concentrated in vacuo. The precipitate was filtered, washed with H$_2$O (10 mL) and dried under high vacuum resulting in compound 15 (700 mg). Method H; Rt: 3.81 min. m/z:845.5 (M+H)$^+$ Exact mass: 844.4; SFC: Column: AS-H 250 mm×4.6 mm; 5 um._Flow: 2.5 mL/min, Mobile phase: A: CO$_2$ B: MeOH (0.05% Diethylamine); 40% B in A,: Rt: 3.84 min; SFC: Column: AS-H 250 mm×4.6 mm; 5 um._Flow: 2.5 mL/min, Mobile phase: A: CO$_2$ B: iPrOH (0.05% Diethylamine); 40% B in A,: Rt: 5.15 min;

BIOLOGICAL EXAMPLES

Anti-HCV Activity of Compounds of Formula I

Replicon Assay

The compounds of formula (I) were examined for inhibitory activity in the HCV replicon. This cellular assay is based on a bicistronic expression construct, as described by Lohmann et al. (Science (1999) 285: 110-113; Journal of Virology (2003) 77: 3007-3019) with modifications described by Krieger et al. (Journal of Virology (2001) 75: 4614-4624), and Lohmann et al. (Journal of Virology (2003) 77: 3007-3019) for genotype 1b and by Yi et al. (Journal of Virology (2004) 78: 7904-7915) for genotype 1a, in a multi-target screening strategy.

Stable Transfection

The method was as follows. The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter portion (FfL-luciferase), and a selectable marker portion (neoR, neomycine phosphotransferase). The construct is flanked by 5' and 3' NTRs (non-translated regions) from HCV type 1b. Continued culture of the replicon cells in the presence of G418 (neoR) is dependent on the replication of the HCV RNA. The stably transfected replicon cells that replicate HCV RNA autonomously and to high levels, encoding inter alia luciferase, were used for screening the antiviral compounds.

The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound was monitored on the Huh-Luc cells, enabling a dose-response curve for each test compound. EC$_{50}$ values were then calculated, which represent the amount of compound required to decrease the level of detected luciferase activity by 50%, or more specifically, to reduce the ability of the genetically linked HCV replicon RNA to replicate.

Results

Where a compound of formula (I) was tested more than once in the replicon assay, the average of all test results is given in this Table 1.

| STRUCTURE | Compound nr. | HCV-REP-HUH7LUC_EC$_{50}$ (nM) |
|---|---|---|
| 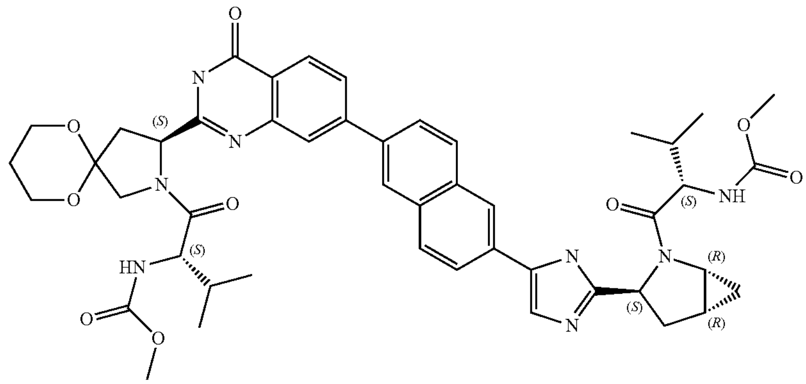 | 1 | 0.026 |
| 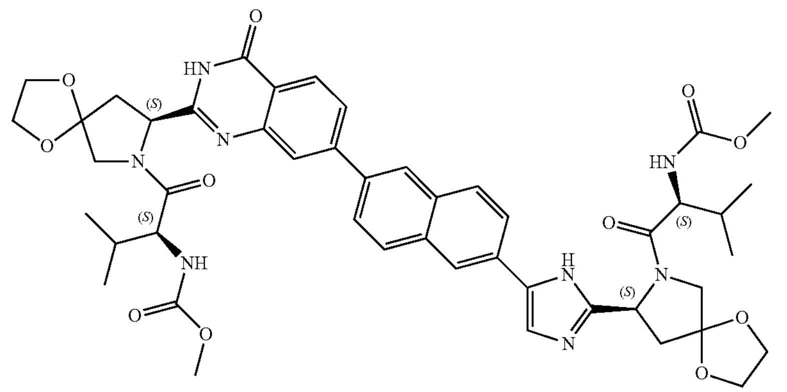 | 2 | 0.018 |
| 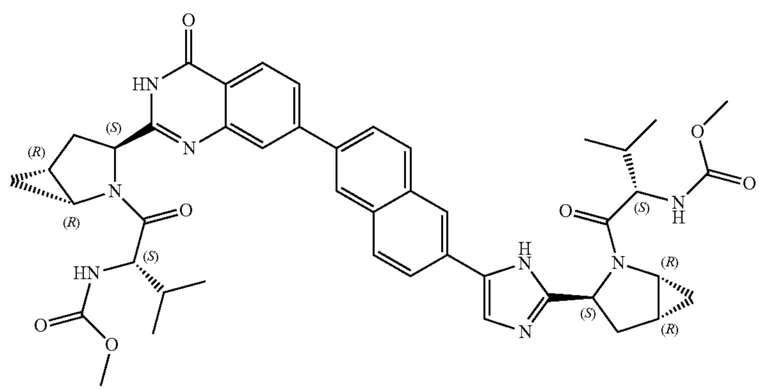 | 3 | 0.017 |
| 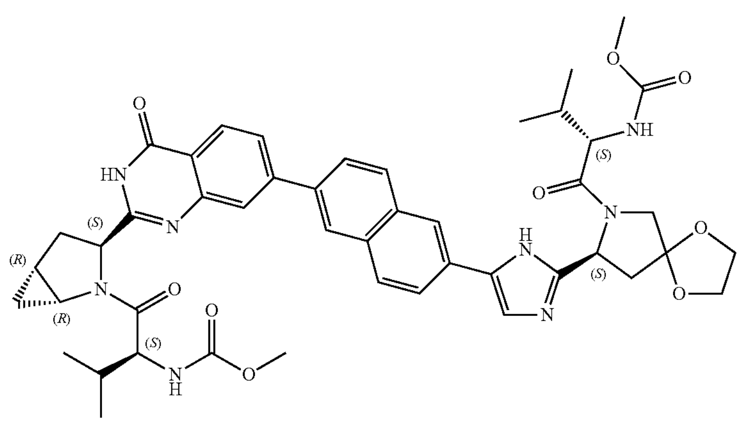 | 4 | 0.008 |

-continued

| STRUCTURE | Compound nr. | HCV-REP-HUH7LUC_EC$_{50}$ (nM) |
|---|---|---|
| 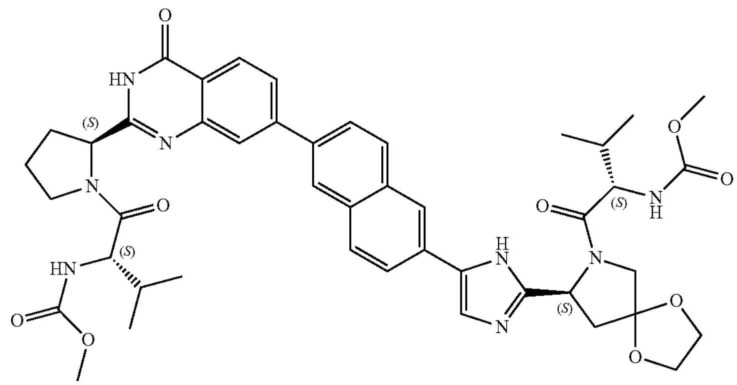 | 5 | 0.025 |
| 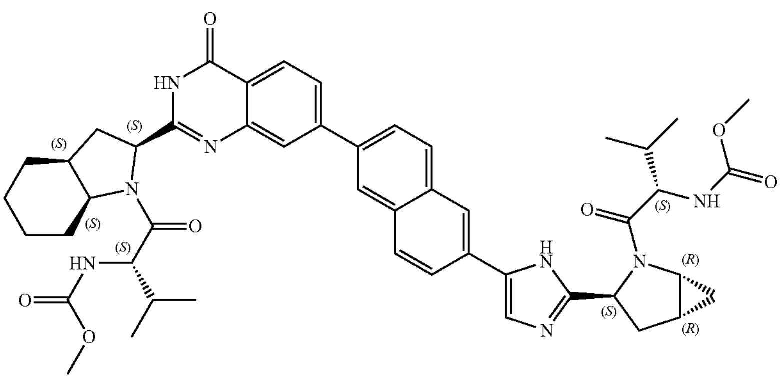 | 7 | 0.008 |
| 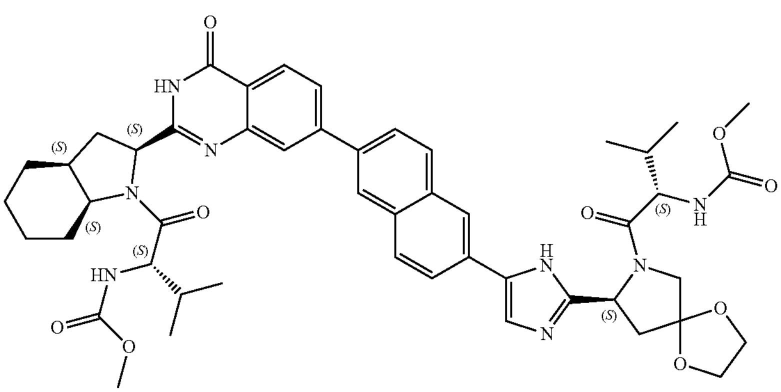 | 9 | 0.008 |
| 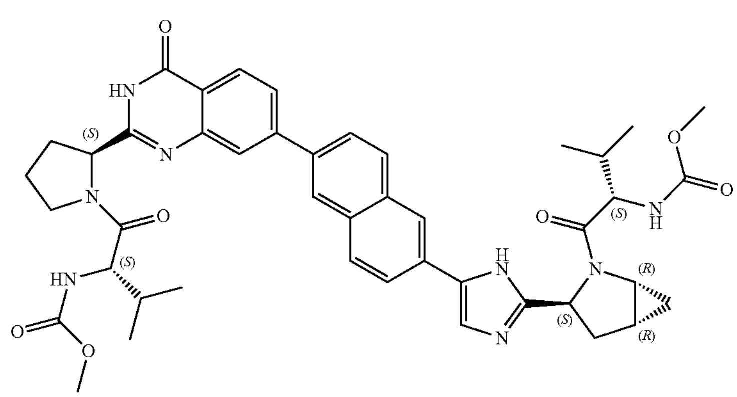 | 10 | 0.006 |

-continued

| STRUCTURE | Compound nr. | HCV-REP-HUH7LUC_EC$_{50}$ (nM) |
|---|---|---|
| 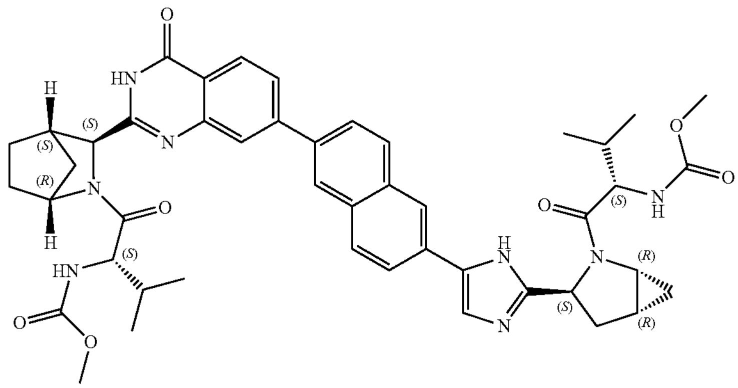 | 12 | 0.27 |
| 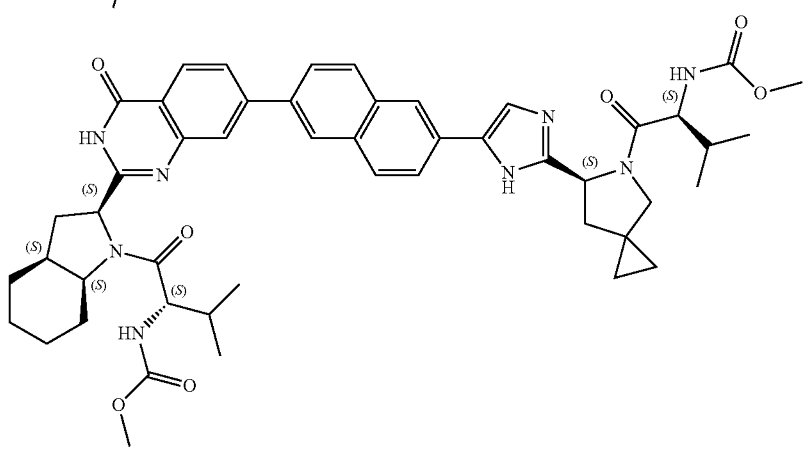 | 13 | 0.006 |
| 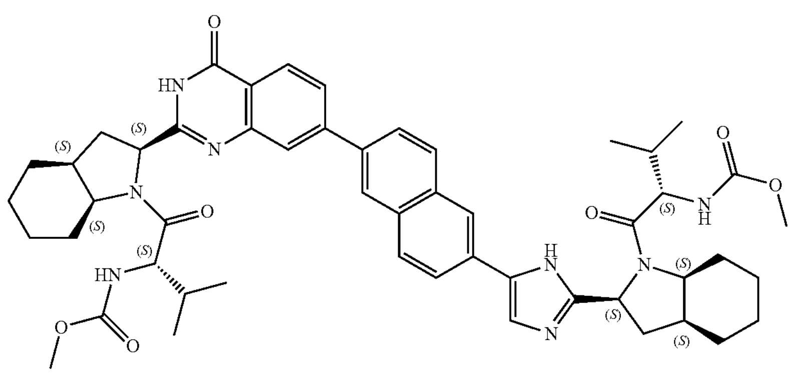 | 14 | 0.022 |
| 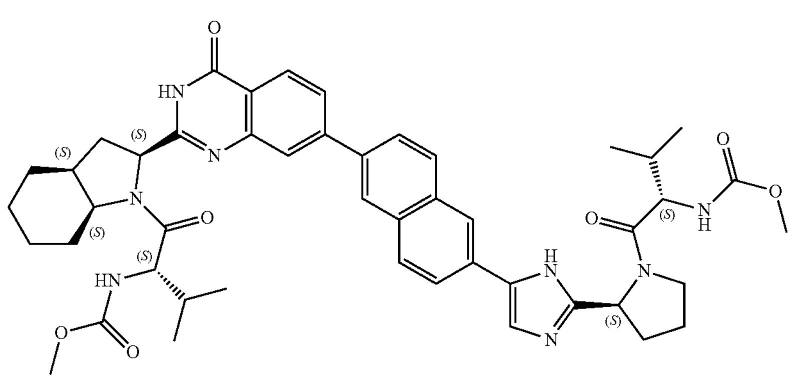 | 15 | 0.006 |

Transient Transfection

In a transient set-up, a Huh-7 lunet hepatoma cell line was transiently transfected with an autonomously replicating RNA encoding a bi-cistronic expression construct. This construct comprises a firefly luciferase reporter gene preceding the NS3-NS5B subgenomic region of HCV (genotype 1a H77 or 1b Con1). Translation of the HCV subgenomic region is mediated by an internal ribosome entry site of encephalomyocarditis virus. The construct is furthermore flanked by 5' and 3' untranslated regions of HCV (genotype 1a H77 or 1b Con1, respectively), which allow for replication of the RNA.

Cells were plated in 384 well plates in the presence of test and control compounds, which were added in various concentrations. Following an incubation of two days, replication of the HCV subgenomic replicon RNA was measured by assaying luciferase activity (using standard luciferase assay substrates and reagents and a Perkin Elmer ViewLux™ ultraHTS microplate imager). HCV subgenomic replicon containing cells in the control cultures have high luciferase expression in the absence of any inhibitor. The inhibitory activity of the compound was monitored, enabling a dose-response curve for each test compound. $EC_{50}$ values were then calculated, which represent the amount of compound required to decrease the level of detected luciferase activity by 50%, or more specifically, to reduce the ability of the genetically linked HCV subgenomic RNA to replicate.

Counterscreens

Counterscreen cell lines included a Huh-7 hepatoma cell line containing a human cytomegalovirus major immediate-early promoter-Luc construct (Huh7-CMV-Luc) and an MT4 T-cell line containing a long terminal repeat-Luc reporter (MT4-LTR-Luc).

| Compound number | 1b $EC_{50}$ (Transient) nM | 1a $EC_{50}$ (Transient) nM | $CC_{50}$ MT4-LTR-luc (µM) | $CC_{50}$ Huh7-CMV-luc (µM) |
| --- | --- | --- | --- | --- |
| 1 | 0.029 | 0.79 | >0.98 | >0.98 |
| 2 | 0.033 | 1.4 | >0.98 | >0.98 |
| 3 | 0.012 | 0.16 | >0.98 | >0.98 |
| 4 | 0.013 | 0.103 | >0.98 | >0.98 |
| 5 | 0.025 | 0.677 | >0.98 | >0.98 |
| 7 | 0.006 | 0.546 | >0.98 | >0.98 |
| 9 | 0.006 | 0.216 | >0.98 | >0.98 |
| 10 | 0.005 | 0.341 | >0.98 | >0.98 |
| 12 | 0.109 | 12.5 | >0.98 | >0.98 |
| 13 | 0.009 | 0.360 | >0.98 | >0.98 |
| 14 | 0.021 | 0.136 | >0.98 | >0.98 |
| 15 | 0.007 | 0.496 | >0.98 | >0.98 |

The invention claimed is:

1. A compound of Formula (I)

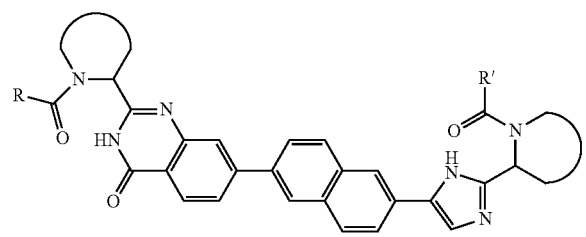
(I)

or a stereoisomer thereof, wherein:

at least one of

independently is selected from a group consisting of

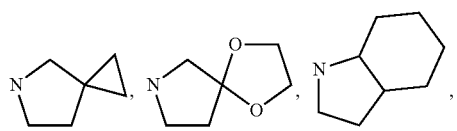

and the other

is independently selected from the group consisting of

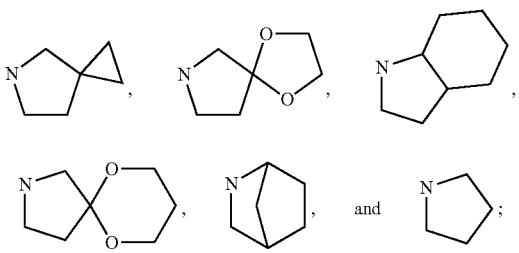

R and R' are independently selected from —$CR_1R_2R_3$, aryl and —$CR_1R_2R_3$ substituted with 1 or 2 substituents selected from halo and methyl, or heterocycloalkyl, wherein $R_1$ is selected from the group consisting of methyl; $C_{2-4}$alkyl, optionally substituted with methoxy or hydroxy; and phenyl, optionally substituted with 1 or 2 substituents independently selected from halo and methyl;

$R_2$ is selected from the group consisting of hydroxy, amino, $C_{1-4}$alkylamino, di-$C_{1-4}$alkylamino, $C_{1-4}$alkylcarbonylamino, and $C_{1-4}$alkyloxycarbonylamino;

$R_3$ is hydrogen or $C_{1-4}$alkyl;

or a pharmaceutically acceptable salt or solvate thereof.

2. The compound according to claim 1, which is of Formula (Ia)

Ia

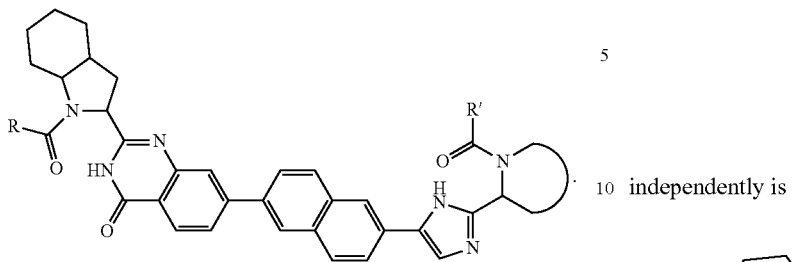

3. The compound of Formula (I) according to claim 1, wherein at least one

independently is selected from the group consisting of

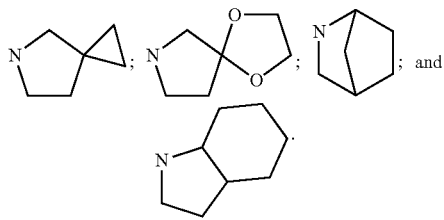

4. The compound of Formula (I) according to claim 1, wherein at least one

independently is

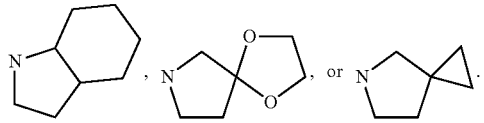

5. The compound according to claim 1, wherein $R_1$ is selected from the group consisting of $C_2$alkyl substituted with methoxy; $C_3$alkyl, optionally substituted with methoxy; branched $C_4$alkyl; and phenyl, optionally substituted with 1 substituent selected from halo and methyl.

6. The compound according to claim 1, wherein $R_2$ is $C_{1-4}$alkylcarbonylamino or $C_{1-4}$alkyloxycarbonylamino; and $R_3$ is hydrogen.

7. A pharmaceutical composition comprising a compound according to claim 1 and a pharmaceutically acceptable carrier.

8. A product containing (a) a compound according to claim 1 and (b) another hepatitis C virus inhibitor.

9. A method for treating a hepatitis C infection in a mammal, comprising administering to said mammal the compound according to claim 1.

* * * * *